(12) United States Patent
Bruton et al.

(10) Patent No.: US 11,800,898 B2
(45) Date of Patent: Oct. 31, 2023

(54) ELECTRONIC AEROSOL PROVISION SYSTEM

(71) Applicant: NICOVENTURES TRADING LIMITED, London (GB)

(72) Inventors: Connor Bruton, London (GB); Colin Dickens, London (GB); Patrick Moloney, London (GB); Anton Korus, Derby (GB); Alfred Vincent Spencer, London (GB); Kevin David Blick, London (GB); Lisa Harvey, London (GB); Anna Azzopardi, London (GB)

(73) Assignee: Nicoventures Trading Limited, London (GB)

( * ) Notice: Subject to any disclaimer, the term of this patent is extended or adjusted under 35 U.S.C. 154(b) by 202 days.

(21) Appl. No.: 15/733,280

(22) PCT Filed: Dec. 19, 2018

(86) PCT No.: PCT/GB2018/053696
§ 371 (c)(1),
(2) Date: Jun. 19, 2020

(87) PCT Pub. No.: WO2019/122880
PCT Pub. Date: Jun. 27, 2019

(65) Prior Publication Data
US 2020/0384220 A1 Dec. 10, 2020

(30) Foreign Application Priority Data
Dec. 20, 2017 (GB) ...................................... 1721477

(51) Int. Cl.
*A61M 15/06* (2006.01)
*A24F 40/50* (2020.01)
(Continued)

(52) U.S. Cl.
CPC .............. *A24F 40/50* (2020.01); *A24F 40/30* (2020.01); *A61M 11/042* (2014.02);
(Continued)

(58) Field of Classification Search
CPC .... A61M 11/042; A61M 15/06; A24B 15/167
See application file for complete search history.

(56) References Cited

U.S. PATENT DOCUMENTS

| 2,250,034 A | 7/1941 | Richard et al. |
| 3,347,231 A | 10/1967 | Chien-Hshuing et al. |
| (Continued) | | |

FOREIGN PATENT DOCUMENTS

| BR | 8201451 A | 7/1982 |
| CA | 2641869 A1 | 5/2010 |
| (Continued) | | |

OTHER PUBLICATIONS

International Search Report and Written Opinion, Application No. PCT/GB2018/053696, dated Mar. 22, 2019, 17 pages.
(Continued)

*Primary Examiner* — Neil Abrams
(74) *Attorney, Agent, or Firm* — Patterson Thuente P.A.

(57) ABSTRACT

Described is an aerosol provision device for generating aerosol from a plurality of aerosol generating areas each configured to receive an aerosol precursor material, wherein the aerosol provision device includes a power source for providing power to a first atomizing element configured to generate aerosol from a first aerosol precursor material present in the first aerosol generating area and to a second atomizing element configured to generate aerosol from a second aerosol precursor material present in a second aerosol generating area; and power distribution circuitry configured to distribute power between the first and second atomizing elements based on at least one parameter of aerosol (Continued)

precursor material currently present in the first and second aerosol generating areas respectively.

21 Claims, 9 Drawing Sheets

(51) Int. Cl.
  *A61M 11/04* (2006.01)
  *A24F 40/30* (2020.01)
  *A24B 15/167* (2020.01)
  *H05B 1/02* (2006.01)
  *A24F 40/10* (2020.01)
  *A24F 40/20* (2020.01)

(52) U.S. Cl.
  CPC ........... *A61M 15/06* (2013.01); *A24B 15/167* (2016.11); *A24F 40/10* (2020.01); *A24F 40/20* (2020.01); *A61M 2205/3653* (2013.01); *A61M 2205/8206* (2013.01); *H05B 1/0244* (2013.01); *H05B 2203/021* (2013.01)

(56) References Cited

U.S. PATENT DOCUMENTS

| | | | |
|---|---|---|---|
| 3,876,363 | A | 4/1975 | La Haye et al. |
| 4,482,315 | A | 11/1984 | Day |
| 5,002,048 | A | 3/1991 | Makiej, Jr. |
| 5,345,951 | A | 9/1994 | Serrano et al. |
| 5,429,122 | A | 7/1995 | Zanen et al. |
| 5,437,267 | A | 8/1995 | Weinstein et al. |
| 5,441,060 | A | 8/1995 | Rose et al. |
| 5,492,112 | A | 2/1996 | Mecikalski et al. |
| 5,743,251 | A | 4/1998 | Howell et al. |
| 5,810,018 | A | 9/1998 | Monte |
| 5,894,841 | A | 4/1999 | Voges |
| 6,325,475 | B1 | 12/2001 | Hayes et al. |
| 6,390,453 | B1 | 5/2002 | Frederickson et al. |
| 6,779,520 | B2 | 8/2004 | Genova et al. |
| 7,305,986 | B1 | 12/2007 | Steiner et al. |
| 9,089,658 | B2 | 7/2015 | Dunne et al. |
| 10,189,632 | B2 * | 1/2019 | Bessant ............... B65D 83/384 |
| 10,251,426 | B2 | 4/2019 | Nielsen |
| 10,306,925 | B2 | 6/2019 | Borkovec et al. |
| 10,368,581 | B2 * | 8/2019 | Rostami ............ A61M 15/0003 |
| 10,433,580 | B2 | 10/2019 | Kobal et al. |
| 10,433,585 | B2 | 10/2019 | Tucker et al. |
| 10,786,010 | B2 | 9/2020 | Hubbard et al. |
| 11,439,183 | B2 * | 9/2022 | Woodcock ........... G08B 21/182 |
| 2003/0106552 | A1 | 6/2003 | Sprinkel, Jr. et al. |
| 2004/0118396 | A1 | 6/2004 | Hughes et al. |
| 2005/0263618 | A1 | 12/2005 | Spallek et al. |
| 2005/0274378 | A1 | 12/2005 | Bonney et al. |
| 2006/0207596 | A1 | 9/2006 | Lane |
| 2006/0231090 | A1 | 10/2006 | King |
| 2007/0062548 | A1 | 3/2007 | Horstmann et al. |
| 2007/0154407 | A1 | 7/2007 | Peters et al. |
| 2008/0223953 | A1 | 9/2008 | Tomono et al. |
| 2008/0241255 | A1 | 10/2008 | Rose et al. |
| 2008/0268060 | A1 | 10/2008 | Nguyen et al. |
| 2009/0266358 | A1 | 10/2009 | Sacristan Rock et al. |
| 2009/0301471 | A1 | 12/2009 | Stirzel |
| 2010/0319686 | A1 | 12/2010 | Schennum |
| 2011/0309157 | A1 | 12/2011 | Yang et al. |
| 2012/0048266 | A1 | 3/2012 | Alelov |
| 2012/0055467 | A1 | 3/2012 | Brambilla et al. |
| 2012/0291791 | A1 | 11/2012 | Pradeep |
| 2013/0056005 | A1 | 3/2013 | Knudsen |
| 2013/0192615 | A1 | 8/2013 | Tucker et al. |
| 2013/0319431 | A1 | 12/2013 | Cyphert et al. |
| 2013/0331771 | A1 | 12/2013 | Kirk et al. |
| 2013/0333700 | A1 | 12/2013 | Buchberger |
| 2013/0340778 | A1 | 12/2013 | Liu |
| 2014/0000638 | A1 | 1/2014 | Sebastian et al. |
| 2014/0060527 | A1 | 3/2014 | Liu |
| 2014/0060554 | A1 | 3/2014 | Collett et al. |
| 2014/0060556 | A1 | 3/2014 | Liu |
| 2014/0083441 | A1 | 3/2014 | Kaplani |
| 2014/0123989 | A1 | 5/2014 | LaMothe |
| 2014/0190503 | A1 | 7/2014 | Li et al. |
| 2014/0224248 | A1 | 8/2014 | Edwards et al. |
| 2014/0261408 | A1 | 9/2014 | DePiano et al. |
| 2014/0261488 | A1 | 9/2014 | Tucker |
| 2014/0261493 | A1 | 9/2014 | Smith et al. |
| 2014/0290650 | A1 | 10/2014 | Ivey |
| 2014/0299142 | A1 | 10/2014 | Dincer et al. |
| 2014/0305429 | A1 | 10/2014 | Lewis |
| 2014/0360514 | A1 | 12/2014 | Zhu |
| 2014/0366898 | A1 | 12/2014 | Monsees et al. |
| 2015/0027454 | A1 | 1/2015 | Li et al. |
| 2015/0040926 | A1 | 2/2015 | Saydar et al. |
| 2015/0047662 | A1 | 2/2015 | Hopps |
| 2015/0053217 | A1 | 2/2015 | Steingraber et al. |
| 2015/0090253 | A1 | 4/2015 | Farrow |
| 2015/0114407 | A1 | 4/2015 | Duncan et al. |
| 2015/0114409 | A1 | 4/2015 | Brammer et al. |
| 2015/0144145 | A1 | 5/2015 | Chang et al. |
| 2015/0164141 | A1 | 6/2015 | Newton |
| 2015/0176436 | A1 | 6/2015 | Palmer |
| 2015/0196055 | A1 | 7/2015 | Liu |
| 2015/0223521 | A1 | 8/2015 | Menting et al. |
| 2015/0245654 | A1 | 9/2015 | Memari et al. |
| 2015/0257447 | A1 | 9/2015 | Sullivan |
| 2015/0257451 | A1 | 9/2015 | Brannon et al. |
| 2015/0258287 | A1 | 9/2015 | Shahaf et al. |
| 2015/0272220 | A1 | 10/2015 | Spinka et al. |
| 2015/0282530 | A1 | 10/2015 | Johnson et al. |
| 2015/0292084 | A1 | 10/2015 | Glaudel et al. |
| 2015/0305406 | A1 | 10/2015 | Li et al. |
| 2015/0313282 | A1 | 11/2015 | Ademe et al. |
| 2016/0089508 | A1 | 3/2016 | Smith et al. |
| 2016/0095357 | A1 | 4/2016 | Burton |
| 2016/0198771 | A1 | 7/2016 | Goggin et al. |
| 2016/0206001 | A1 | 7/2016 | Eng et al. |
| 2016/0235121 | A1 | 8/2016 | Rogan et al. |
| 2016/0262454 | A1 | 9/2016 | Sears et al. |
| 2016/0309782 | A1 | 10/2016 | Malgat et al. |
| 2016/0330999 | A1 | 11/2016 | Cameron |
| 2016/0331026 | A1 * | 11/2016 | Cameron ............... A24F 40/50 |
| 2016/0338407 | A1 | 11/2016 | Kerdemelidis |
| 2016/0356751 | A1 | 12/2016 | Blackley |
| 2016/0360791 | A1 | 12/2016 | Blackley |
| 2016/0361452 | A1 | 12/2016 | Blackley |
| 2016/0361677 | A1 | 12/2016 | Blackley |
| 2016/0361678 | A1 | 12/2016 | Blackley |
| 2016/0361972 | A1 | 12/2016 | Blackley |
| 2016/0363332 | A1 | 12/2016 | Blackley |
| 2016/0363339 | A1 | 12/2016 | Blackley |
| 2016/0363567 | A1 | 12/2016 | Blackley |
| 2016/0363570 | A1 | 12/2016 | Blackley |
| 2016/0363582 | A1 | 12/2016 | Blackley |
| 2016/0363917 | A1 | 12/2016 | Blackley |
| 2016/0374401 | A1 | 12/2016 | Liu |
| 2017/0027232 | A1 | 2/2017 | Aleandre |
| 2017/0064994 | A1 | 3/2017 | Xu et al. |
| 2017/0095004 | A1 | 4/2017 | Liu |
| 2017/0135406 | A1 * | 5/2017 | Reevell ................. H05B 3/04 |
| 2017/0150755 | A1 | 6/2017 | Nuno |
| 2017/0251721 | A1 | 9/2017 | Rostami |
| 2017/0251726 | A1 | 9/2017 | Nielsen |
| 2017/0251727 | A1 | 9/2017 | Nielsen |
| 2017/0295849 | A1 | 10/2017 | Cadieux et al. |
| 2017/0360981 | A1 | 12/2017 | Avidor |
| 2018/0271170 | A1 | 9/2018 | Tucker et al. |
| 2018/0325176 | A1 * | 11/2018 | Burseg ................. A24F 40/50 |
| 2019/0000147 | A1 | 1/2019 | Koc et al. |
| 2019/0320718 | A1 | 10/2019 | Yilmaz et al. |

(56) References Cited

U.S. PATENT DOCUMENTS

| | | | |
|---|---|---|---|
| 2019/0357596 A1 | 11/2019 | Blick et al. | |
| 2020/0384220 A1* | 12/2020 | Bruton | A61M 15/06 |

FOREIGN PATENT DOCUMENTS

| | | |
|---|---|---|
| CN | 1362609 A | 8/2002 |
| CN | 2610293 Y | 4/2004 |
| CN | 200975836 Y | 11/2007 |
| CN | 201302362 Y | 9/2009 |
| CN | 202738816 U | 2/2013 |
| CN | 203378558 U | 1/2014 |
| CN | 103783673 A | 5/2014 |
| CN | 203789150 U | 8/2014 |
| CN | 203860452 U | 10/2014 |
| CN | 203873006 U | 10/2014 |
| CN | 203884699 U | 10/2014 |
| CN | 203952438 U | 11/2014 |
| CN | 203986105 U | 12/2014 |
| CN | 204104836 U | 1/2015 |
| CN | 204104837 U | 1/2015 |
| CN | 204104838 U | 1/2015 |
| CN | 204120239 U | 1/2015 |
| CN | 204146323 U | 2/2015 |
| CN | 104397876 A | 3/2015 |
| CN | 204217914 U | 3/2015 |
| CN | 204245158 U | 4/2015 |
| CN | 204273248 U | 4/2015 |
| CN | 204351068 U | 5/2015 |
| CN | 204617067 U | 9/2015 |
| CN | 204653784 U | 9/2015 |
| CN | 104957773 A | 10/2015 |
| CN | 105852222 A | 8/2016 |
| CN | 106455696 A | 2/2017 |
| CN | 205947119 U | 2/2017 |
| CN | 106604755 A | 4/2017 |
| EP | 3170413 | 5/2014 |
| EP | 2754361 A1 | 7/2014 |
| EP | 2989912 A1 | 3/2016 |
| EP | 3235390 A1 | 10/2017 |
| EP | 3287020 A1 | 2/2018 |
| EP | 3727061 A1 | 10/2020 |
| GB | 444944 A | 3/1936 |
| GB | 1271485 A | 4/1972 |
| GB | 2388040 A | 11/2003 |
| GB | 2515562 A | 12/2014 |
| GB | 2522395 A | 7/2015 |
| GB | 2524779 | 10/2015 |
| JP | S59232082 A | 12/1984 |
| JP | H03105299 U | 10/1991 |
| JP | 2007136451 A | 6/2007 |
| JP | 2011518638 A | 6/2011 |
| KR | 200454619 Y1 | 7/2011 |
| KR | 20140118985 A | 10/2014 |
| KR | 20160112770 A | 9/2016 |
| RU | 2509516 C2 | 3/2014 |
| RU | 2592163 C1 | 7/2016 |
| RU | 2597540 C2 | 9/2016 |
| RU | 2606072 C2 | 1/2017 |
| RU | 2608277 C2 | 1/2017 |
| WO | WO-2007143993 A2 | 12/2007 |
| WO | WO-2010045408 A2 | 4/2010 |
| WO | WO-2010052323 A2 | 5/2010 |
| WO | WO-2011015850 A1 | 2/2011 |
| WO | WO-2012174677 A1 | 12/2012 |
| WO | WO-2013076750 A1 | 5/2013 |
| WO | WO-2013113173 A1 | 8/2013 |
| WO | WO 2013/152873 | 10/2013 |
| WO | WO-2014012840 A2 | 1/2014 |
| WO | WO-2014012841 A2 | 1/2014 |
| WO | WO-2014016961 A1 | 1/2014 |
| WO | WO-2014020539 A1 | 2/2014 |
| WO | WO-2014038484 A1 | 3/2014 |
| WO | WO-2014110119 A1 | 7/2014 |
| WO | WO-2014110750 A1 | 7/2014 |
| WO | WO-2014115324 A1 | 7/2014 |
| WO | WO-2014139611 A1 | 9/2014 |
| WO | WO-2014140320 A1 | 9/2014 |
| WO | WO-2014187763 A1 | 11/2014 |
| WO | WO-2014195250 A1 | 12/2014 |
| WO | WO-2015000974 A1 | 1/2015 |
| WO | WO-2015015431 A1 | 2/2015 |
| WO | WO-2015027470 A1 | 3/2015 |
| WO | WO-2015038981 A2 | 3/2015 |
| WO | WO-2015052192 A1 | 4/2015 |
| WO | WO-2015079197 A1 | 6/2015 |
| WO | WO-2015079198 A1 | 6/2015 |
| WO | WO-2015109532 A1 | 7/2015 |
| WO | WO-2015124807 A1 | 8/2015 |
| WO | WO-2015127663 A1 | 9/2015 |
| WO | WO-2015139338 A1 | 9/2015 |
| WO | WO-2015149647 A1 | 10/2015 |
| WO | WO-2015165146 A1 | 11/2015 |
| WO | WO-2015166952 A1 | 11/2015 |
| WO | WO-2015189556 A1 | 12/2015 |
| WO | 2016001926 A1 | 1/2016 |
| WO | WO-2016009202 A1 | 1/2016 |
| WO | WO-2016014652 A1 | 1/2016 |
| WO | WO-2016030661 A1 | 3/2016 |
| WO | WO16050247 | 4/2016 |
| WO | WO-2016050244 A1 | 4/2016 |
| WO | WO-2016054476 A1 | 4/2016 |
| WO | WO-2016075748 A1 | 5/2016 |
| WO | WO16090426 | 6/2016 |
| WO | WO-2017032695 A1 | 3/2017 |
| WO | WO-2017122196 A1 | 7/2017 |
| WO | WO-2017153591 A1 | 9/2017 |
| WO | WO 2017/185051 | 10/2017 |
| WO | 2017206480 A1 | 12/2017 |
| WO | WO 2018/146453 | 8/2018 |
| WO | 2019122878 A1 | 6/2019 |

OTHER PUBLICATIONS

Communication pursuant to Article 94 (3) EPC for Application No. 18829447.4, dated Oct. 25, 2021, 15 pages.

Communication pursuant to Article 94 (3) EPC for Application No. 18829448.2, dated Oct. 28, 2021, 26 pages.

Craze, "http://www.crazeeshisha.com/home", Aug. 8, 2019, 1 page.

Decision Grant dated Nov. 27, 2019 for Russian Application No. RU2019125262, 14 pages.

ECIG VAPGO, "Mega Twix Dual Tank Clearomizer 3.6 ml, as available at https://www.ecig-vapo.com/mega-twix-dual-tank-clearomizer-36ml-p-911.html", 2 pages.

First Union, "Dual Tank 240 ISMK Clearomizer retrieved on Aug. 8, 2019 at http://www.chinafirstunion.com/product/Dual-Tank-240.html", May 8, 2015, 2 pages.

International Preliminary Report on Patentability for Application No. PCT/GB2018/050262, dated Aug. 22, 2019, 7 pages.

International Search Report and Written Opinion for Application No. PCT/GB2018/050266, dated Apr. 20, 2018, 8 pages.

International Preliminary Report on Patentability for Application No. PCT/GB2018/050266, dated May 17, 2019, 12 pages.

International Preliminary Report on Patentability for Application No. PCT/GB2018/053694, dated Mar. 11, 2020, 7 pages.

International Preliminary Report on Patentability for Application No. PCT/GB2018/053696, dated Jul. 2, 2020, 10 pages.

International Search Report and Written Opinion, Application No. PCT/GB2018/053694, dated Mar. 21, 2019, 13 pages.

International Search Report and Written Opinion for Application No. PCT/GB2018/050262, dated Apr. 20, 2018, 12 pages.

Kik Dual Tank- Dual Flavour Clearomizer dated Apr. 3, 2015 and retrieved on Aug. 8, 2019 at http://www.kik.co.uk/kik-dual-tank-dual-flavourclearomizer, 2 pages.

Notice of Reason for Refusal for Japanese Application No. 2019-539197 dated Nov. 10, 2020, 8 pages.

Notice of Reasons for Rejection for Japanese Application No. 2020-529273, dated Jun. 8, 2021, 8 pages.

Office Action and Search Report dated Jul. 17, 2019 for Chinese Application No. 201680053577.6, 46 pages.

(56) References Cited

OTHER PUBLICATIONS

Office Action for Japanese Application No. 2020-528342, dated Aug. 3, 2021, 13 pages.
Office Action for Korean Application No. 10-2019-7023028, dated Dec. 22, 2020, 15 pages.
Office Action for Korean Application No. 10-2019-7023028, dated Jun. 24, 2021, 3 pages.
Osboo, "Dual Tank 240 Clearomizer," dated Dec. 31, 2016 and retrieved on Aug. 8, 2019 at http://www.osboo.co.uk/products/accessories/dual-tank-240-clearomizer/, 1 page.
Prestige Vaping Premium Electronic Cigarettes, Dual Tank Dual Flavour Clearomizer, dated Apr. 19, 2015 and retrieved on Aug. 8, 2019 at http://prestigevaping.co.uk/dual-tank-clearomizer, 1 page.
Search Report for Russian Application No. 2020120155 dated Nov. 2, 2020, 2 pages.
Search Report for Russian Application No. 2020120336 dated Mar. 2, 2021, 2 pages.
Totally Wicked, "Revolver Atomizer Tank", dated Sep. 12, 2015 and retrieved on Aug. 8, 2019 at http://www.totallywicked-eliquid.co.uk/products/replacement-coil-systems-2/replacement-coil-systems/view-all/revolver-atomizer-tank-product.html, 2 pages.
UK ECIG Store, "Dark Ronin Modz Dual Triton Box Mod," retrieved on Aug. 8, 2019 at https://www.ukecigstore.com/dark-ronin-modz-dual-triton-box-mod.html, 1 page.
Office Action for Canadian Application No. 3,085,971, dated Apr. 28, 2022, 7 pages.
International Preliminary Report on Patentability received for PCT Patent Application No. PCT/GB2018/053692, dated Mar. 11, 2020, 7 pages.
International Search Report and Written Opinion received for PCT Patent Application No. PCT/GB2018/053692, dated Mar. 21, 2019, 11 pages.
Office Action received for Chinese Patent Application No. 201880082757.6, dated Mar. 3, 2023, 19 pages (8 pages of English Translation and 11 pages of Official Copy).
Office Action received for Chinese Patent Application No. 201880082829.7, dated Mar. 3, 2023, 10 pages (8 pages of English Translation and 2 pages of Official Copy).

* cited by examiner

ELECTRONIC AEROSOL PROVISION SYSTEM

PRIORITY CLAIM

The present application is a National Phase entry of PCT Application No. PCT/GB2018/053696, filed Dec. 19, 2018, which claims priority from GB Patent Application No. 1721477.6, filed Dec. 20, 2017, each of which is hereby fully incorporated herein by reference.

FIELD

The present disclosure relates to electronic aerosol provision systems such as nicotine delivery systems (e.g. electronic cigarettes and the like).

BACKGROUND

Electronic aerosol provision systems such as electronic cigarettes (e-cigarettes) generally contain an aerosol (or vapour) precursor/forming material, such as a reservoir of a source liquid containing a formulation, typically comprising at least one of a base liquid with additives such as nicotine and often flavorants, and/or a solid material such as a tobacco-based product, from which an aerosol is generated, e.g. through heat vaporization. Thus, an aerosol provision system will typically comprise an aerosol generation chamber containing an atomizer (or vaporizer), e.g. a heating element, arranged to vaporize a portion of precursor material to generate an aerosol in the aerosol generation chamber. As a user inhales on the device and electrical power is supplied to the heating element, air is drawn into the device through inlet holes and into the aerosol generation chamber where the air mixes with the vaporized precursor material to form an aerosol. There is a flow path connecting the aerosol generation chamber with an opening in the mouthpiece so the incoming air drawn through the aerosol generation chamber continues along the flow path to the mouthpiece opening, carrying some of the vapor with it, and out through the mouthpiece opening for inhalation by the user.

Aerosol provision systems may comprise a modular assembly including both reusable and replaceable cartridge parts. Typically a cartridge part will comprise at least one of the consumable aerosol precursor material and/or the vaporizer, while a reusable device part will comprise longer-life items, such as a rechargeable battery, device control circuitry, activation sensors, and user interface features. The reusable part may also be referred to as a control unit or battery section, and replaceable cartridge parts that include both a vaporizer and precursor material may also be referred to as cartomizers.

Some aerosol provision systems may include multiple aerosol sources which can be used to generate vapor/aerosol that is mixed and inhaled by a user. However, in some cases, a user may desire a more flexible system in terms of the composition of the aerosol that is delivered to the user and/or how the aerosol is delivered.

Various approaches are described which seek to help address some of these issues.

SUMMARY

According to a first aspect of certain embodiments, there is provided an aerosol provision device for generating aerosol from a plurality of aerosol generating areas, each configured to receive an aerosol precursor material, wherein the aerosol provision device comprises: a power source for providing power to a first atomizing element configured to generate aerosol from a first aerosol precursor material present in the first aerosol generating area and to a second atomizing element configured to generate aerosol from a second aerosol precursor material present in a second aerosol generating area; and power distribution circuitry configured to distribute power between the first and second atomizing elements based on at least one parameter of aerosol precursor material currently present in the first and second aerosol generating areas, respectively.

According to a second aspect of certain embodiments, there is provided an aerosol provision system for generating aerosol from a plurality of aerosol generating areas[,] each configured to receive an aerosol precursor material, the system comprising: the aerosol provision device of the first aspect; and a first aerosol precursor material, wherein the first aerosol precursor material is located in the first aerosol generating area.

According to a third aspect of certain embodiments, there is provided a method of power distribution in an aerosol provision device for generating aerosol from a first aerosol generating area configured to receive a first aerosol precursor material and a second aerosol generating area configured to receive a second aerosol precursor material, the method comprising: receiving an indication of at least one parameter of the quantity of aerosol precursor material currently present in the first and/or second aerosol generating areas respectively; and distributing power between a first atomization element configured to generate aerosol from the first aerosol precursor material and a second atomization element configured to generate aerosol from the second aerosol precursor material based on the received indication.

According to a fourth aspect of certain embodiments, there is provided an aerosol provision means for generating aerosol from a plurality of storage means, each configured to receive an aerosol precursor material, wherein the aerosol provision means comprises: power means for providing power to a first atomizing means configured to generate aerosol from a first aerosol precursor material present in the first storage means and to a second atomizing means configured to generate aerosol from a second aerosol precursor material present in a second storage means; and power distribution means configured to distribute power between the first and second atomizing means based on at least one parameter of aerosol precursor material currently present in the first and second storage means, respectively.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to vapor provision systems, which may also be referred to as aerosol provision systems, such as e-cigarettes. Throughout the following description the term "e-cigarette" or "electronic cigarette" may sometimes be used; however, it will be appreciated this term may be used interchangeably with vapor provision system and electronic vapor provision system. Furthermore, and as is common in the technical field, the terms "vapor" and "aerosol", and related terms such as "vaporize[,]" "volatilize" and "aerosolize," may also be used interchangeably. In this regard, means of generating an aerosol other than via a condensation aerosol are envisaged, such as atomization via vibrational, photonic, irradiative, electrostatic means, etc.

Figure 1:
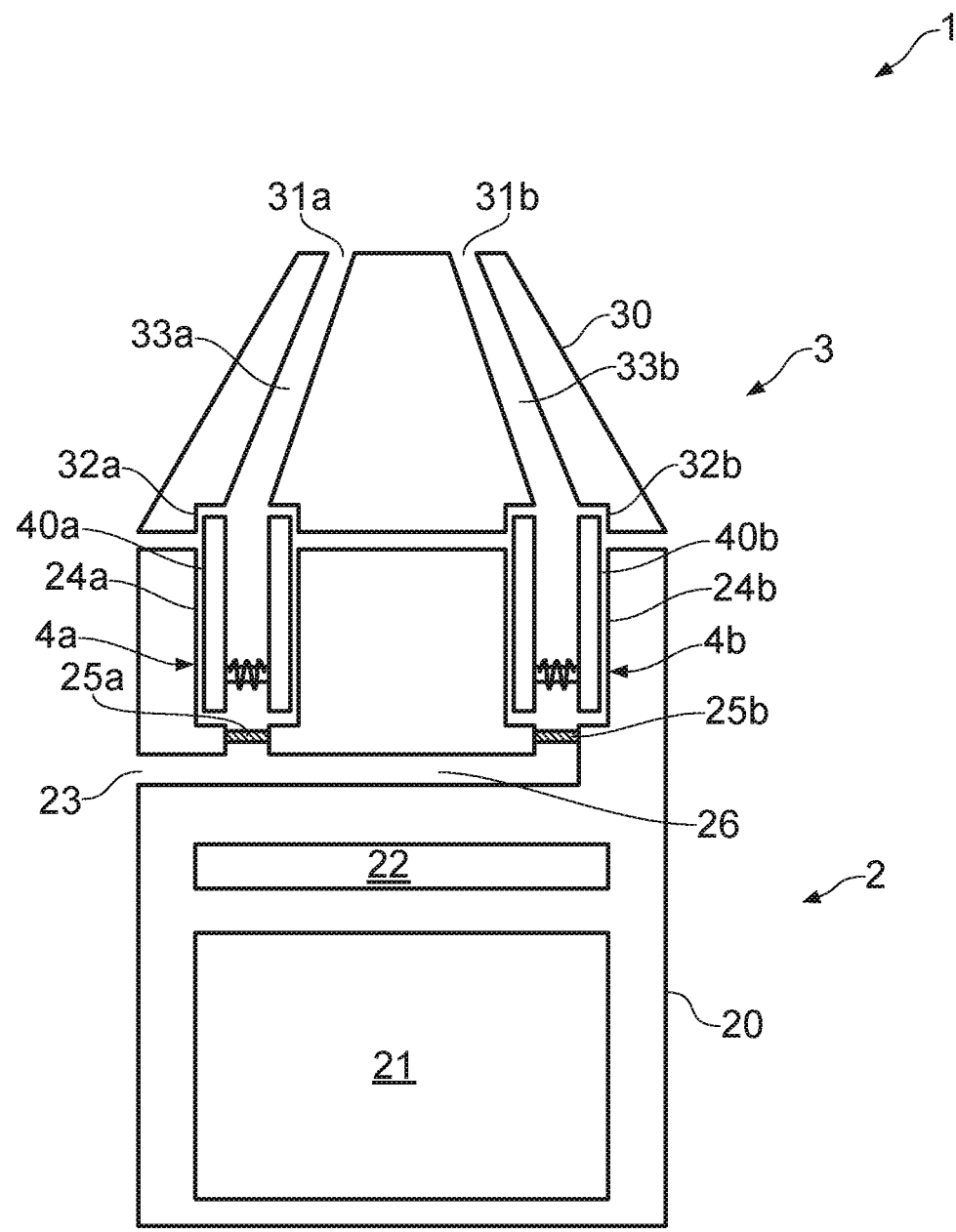
FIG. 1 schematically shows an aerosol delivery system in cross-section, the aerosol delivery system including a control part, a mouthpiece part, and two removable cartomizers, and configured to deliver aerosol to a user from one or more of the cartomizers.
Figure 2:
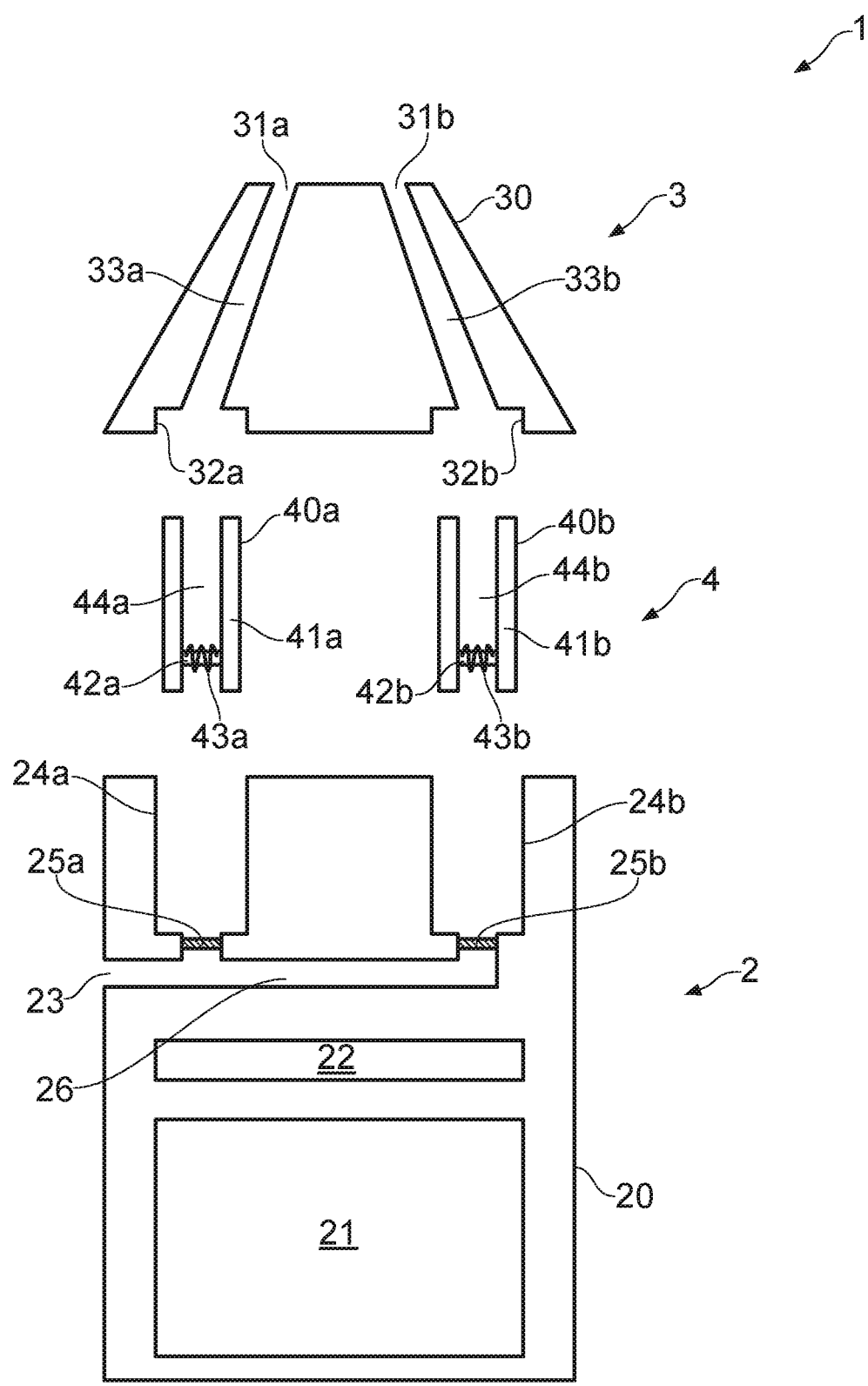
FIG. 2 schematically shows, in cross-section, the aerosol delivery system of FIG. 1 in exploded form showing the individual constituents of the aerosol delivery system.

FIGS. 1 and 2 are highly schematic cross-sectional views of an example aerosol provision system 1 in accordance with some embodiments of the disclosure. FIG. 1 shows the aerosol provision system 1 in an assembled state while FIG. 2 shows the aerosol provision system 1 in a disassembled state/partially exploded state. As will be discussed below, parts of the example aerosol provision system 1 are provided as removable/detachable from other parts of the aerosol provision system 1.

With reference to FIGS. 1 and 2, the example aerosol provision system 1 comprises a control/device (or battery/reusable) part 2, a detachable mouthpiece (or lid) part 3, and, in this example, two aerosol generating components, such as cartomizers 4a and 4b, collectively referred to herein as cartomizers 4. In use, the aerosol provision system 1 is configured to generate aerosol from the cartomizers 4 (by vaporizing an aerosol precursor material) and deliver/provide the aerosol to a user through the mouthpiece part 3 as the user inhales through the mouthpiece part 3. It should be appreciated that the aerosol provision system 1 includes the cartomizers 4 in addition to the control part 2 and mouthpiece part 3. Strictly speaking, the term aerosol provision device refers to just the control/device part 2 and mouthpiece part 3 without the cartomizers 4. However, to aid in the general explanation of the system disclosed, the terms "system" and "device" are used interchangeably herein to refer to either of the device including cartomizers and the device excluding cartomizers.

One aspect of the example aerosol provision system is the functionality of providing consistent delivery of aerosol to the user regardless of the state/configuration of the aerosol provision system. By this, and as will become apparent from below, it is meant that whether a user uses the device with multiple aerosol generating components, e.g. two cartomizers 4, or only a single aerosol generating component, e.g., a single cartomizer 4, the aerosol provision system is controlled to provide a consistent (or close to consistent) experience to the user. This may be in terms of the quantity of aerosol produced (i.e., the quantity/volume of aerosol inhaled) or by providing a generally consistent ratio of vapor to air (i.e., the percentage of vapor contained within the generated aerosol). That is, the quantity of aerosol produced or the ratio of vapor to air is the same (or approximately the same, e.g., within 10%) whether the aerosol provision device has one or multiple aerosol generating components present in the aerosol generating areas. In some implementations, it should be appreciated that the quantity of aerosol produced may vary depending on the strength of the user's inhalation (or puff). For example a stronger puff may generate more aerosol as compared to a weaker puff. However, one aspect of the present disclosure is to ensure little or no variation in expected performance in terms of at least one of quantity of aerosol generated, or the quality of aerosol generated. In this regard, one aspect of the present disclosure is to ensure that the aerosol provision system is able to react to a state of an aerosol generation component of the aerosol provision system.

A further aspect of the example aerosol provision system is the functionality of providing different proportions of aerosol received/inhaled by the user. In this regard, the user may inhale an aerosol comprising different percentages of vapor generated from the aerosol generating components, e.g. cartomizers, located in the device. This may be based on the type of aerosol precursor material forming the aerosol generating components or within the aerosol generating components, for example when the aerosol generating components are cartomizers. The relative proportions may be altered by altering the airflow through each aerosol generating area within the device.

A further aspect of the example aerosol provision system is the ability to control how the aerosol precursor material is used-up (depleted) such that the aerosol precursor material stored within each of a plurality of aerosol generating components, e.g. cartomizers, is completely used-up (or depleted) at the same time in the future. This can ensure that the user does not use-up one of the aerosol generating components, e.g. cartridges, before the other, meaning that the user does not experience an undesired taste caused e.g., by the burning/heating of a dry wicking material resulting from an aerosol precursor material which has been completely (or almost) used up in one aerosol generating area and not another, and also that the user can replace both aerosol generating components, e.g. cartomizers, at the same time therefore minimizing the user's interaction with the device 1 when replenishing the aerosol precursor materials. This can be realized by altering the power distributed to each of the atomizing units designated for the respective aerosol generating areas (whether these form part of the aerosol generating component, or not). For example, when the aerosol generating component comprises a cartomizer having an atomizing unit, this may include increasing the power supplied to the cartomizer having the smallest quantity of aerosol precursor and/or decreasing the power supplied to the cartomizer having the greatest quantity of aerosol precursor.

A further aspect of the example aerosol provision system is the ability to keep different aerosol pathways separate from one another and allow mixing of the different aerosols to occur in the user's mouth. For example, this may be in relation to different flavored aerosols, where each cartomizer 4 contains its own source liquid producing a different flavor (e.g., strawberry flavor and raspberry flavor), and thus the different flavored aerosols are kept separate/isolated from one another within the aerosol provision system 1 itself. This can provide a different sensorial experience to the user and may lead to less "blurring" of the flavors (in other words, the user may be able to identify the individual flavors more readily when each aerosol/vapor is provided directly to the mouth cavity compared to an aerosol mixed in the device). Moreover, the different aerosols may not experience substantial mixing even when leaving the device and effectively be deposited in different regions of the mouth (e.g., on a left and right side of mouth, or on the roof of the mouth and the tongue, etc.) meaning that it is the user themselves who performs the mixing. The device may further be configured to target the different aerosol to different parts of the mouth/mouth cavity, as different flavors may be more or less perceptible to certain areas of the mouth/mouth cavity.

By way of reference only, the following discussion will refer to top, bottom, left, and right sides of the system. This will generally refer to the corresponding directions in the associated figures; that is, the natural directions in the plane of the figures. However, these directions are not meant to confer a particular orientation of the system 1 during normal use. For example, the top of the assembled system refers to a part of the system that contacts the user's mouth in use, while the bottom refers to the opposite end of the system. The choice of directions is only meant to illustrate the relative locations of the various features described herein.

Turning back to FIGS. 1 and 2, the control part 2 includes a housing 20 which is configured to house a power source 21 for providing operating power for the aerosol provision device 1 and control circuitry 22 for controlling and monitoring the operation of the aerosol delivery device 1. In this example, the power source 21 comprises a battery that is rechargeable and may be of a conventional type, for example of the kind normally used in electronic cigarettes and other applications requiring provision of relatively high currents over relatively short periods.

The outer housing 20 may be formed, for example, from a plastics or metallic material and in this example has a generally rectangular cross section with a width (in the plane of FIG. 1) of around 1.5 to 2 times its thickness (perpendicular to the plane of FIG. 1). For example, the electronic cigarette may have a width of around 5 cm and a thickness of around 3 cm. The control part 2 takes the form of a box/cuboid, in this example, although it should be appreciated that the control part 2 can have other shapes as desired.

The control part 2 further comprises an air inlet 23 provided on/in the outer surface of the housing 20, two discrete aerosol generating areas, e.g. receptacles, 24a and 24b each defining a space/volume for receiving one of the aerosol generating components, e.g. cartomizers 4, an air channel 26 which extends into the housing 20 and fluidly connects the air inlet 23 with the receptacles 24a and 24b, and two flow restriction members 25 provided within the air channel 26 at positions where each can vary the airflow into respective receptacles 24a, 24b (specifically in this example at or close to the entrance to the spaces defined by the receptacles 24a, 24b). As will be appreciated in the following these features form part of an air or aerosol pathway through the aerosol provision device 1 in which air is passed from outside the aerosol provision device 1 via air inlet 23, through the aerosol generating areas/receptacles 24a and 24b containing cartomizers 4 and into the user's mouth. Turning now to the cartomizers, the cartomizers 4 each comprise a housing 40a, 40b, which defines a liquid reservoir 41a, 41b that stores a source liquid for vaporization, and a cartomizer channel 44a, 44b, and an atomization unit (or vaporizer) which in this example is formed of a wicking element 42a, 42b and a heating element 43a, 43b coiled around the wicking element 42a, 42b. The wicking elements 42a, 42b are configured to wick/transport a source liquid (using the capillary motion) from the respective liquid reservoirs 41a, 41b to the respective heating elements 43a, 43b.

In the example shown, the atomization units are provided in the respective cartomizer channels 44a, 44b defined by the housing 40a, 40b of the cartomizers 4. The cartomizer channels 44a and 44b are arranged such that, when the cartomizers 4 are installed in respective receptacles, the cartomizer channels 44*a* and 44*b* are fluidly communicated with the air channel 26 and air inlet 23, and thus air drawn in through the air inlet 23 passes along the air channel 26 and along cartomizer channels 44*a* and 44*b* of the cartomizers 4.

As used herein, the term "aerosol generating component" refers to a component that is responsible for generating aerosol. In FIGS. 1 and 2, this includes the cartomizers 4 which comprise both a source liquid (or aerosol forming material) and an atomization unit. In this arrangement, the cartomizers 4 are considered the aerosol generating component because without the cartomizers 4 installed in the system (and/or cartomizers comprising source liquid), aerosol cannot be generated. Moreover, the term "aerosol generating area" refers to an area/region within the system in which aerosol is or can be generated. For instance, in FIGS. 1 and 2, the aerosol generating area includes receptacles 24*a* and 24*b*, which are configured to receive the cartomizers 4. In other words, the cartomizers are considered as the components responsible for generating aerosol, whereas the receptacles house the aerosol generating components and thus define an area where aerosol is generated.

The mouthpiece part 3 includes a housing 30 which comprises two openings 31*a*, 31*b* at one end (a top end); that is, the mouthpiece openings are located at the same end of the mouthpiece part 3 and are generally arranged such that a user can place their mouth over both of the openings. The mouthpiece part 3 also includes receptacles 32*a*, 32*b* at the opposite end (a bottom end), and respective mouthpiece channels 33*a*, 33*b* extending between the receptacles 32*a*, 32*b* and the openings 31*a*, 31*b*.

The mouthpiece part 3 has a generally tapered or pyramidal outer profile which tapers towards the top end of the mouthpiece part 3. The bottom end of the mouthpiece part 3 is where the mouthpiece part 3 and control unit 2 meet or interface and is sized to have dimensions in the width direction (i.e., in the horizontal direction of the plane of FIGS. 1 and 2) and thickness direction (i.e., in a direction orthogonal to the plane of FIGS. 1 and 2) that broadly correspond to equivalent dimensions of the control part 2 in order to provide a flush outer profile when the control part 2 and the mouthpiece part 3 are coupled together. The end of the mouthpiece part 3 in which the openings 31 are located (top end) is smaller in the width direction than the bottom end by around one third (e.g. to around 2 cm wide). That is, the mouthpiece part 3 tapers in the width direction towards the top end. This end forms the part of the aerosol provision device 1 that is received in the user's mouth (in other words, this is the end the user would normally put their lips around and inhale through).

The mouthpiece part 3 is formed as a separate and removable component from the control part 2 and is provided with any suitable coupling/mounting mechanism that allows the mouthpiece part 3 to couple to the control part 2, e.g., snap-fitting, screw thread, etc. When the mouthpiece part 3 is coupled to the control part 2 to form the assembled aerosol provision device 1 (e.g., as generally shown in FIG. 1), the length of the assembled aerosol provision device 1 is around 10 cm. However, it will be appreciated that the overall shape and scale of an aerosol provision device 1 implementing the present disclosure is not significant to the principles described herein.

The receptacles 32*a*, 32*b* are arranged to fluidly connect to the cartomizer channel 44*a* and 44*b* in the cartomizers 4 respectively (specifically at an end of the cartomizer opposite the end that connects to and is received in receptacles 24*a*, 24*b*). The receptacles 32*a*, 32*b* are fluidly connected to mouthpiece channels 33*a* and 33*b* which in turn are fluidly connected to openings 31*a* and 31*b*. Therefore, it should be appreciated that when the device 1 is fully assembled (e.g., as shown in FIG. 1), the openings 31*a* and 31*b* of the mouthpiece part 3 are fluidly connected to air inlet 23 in the control part 2.

Hence, the example aerosol provision device 1 generally provides two routes through which air/aerosol may pass through the device. For example, a first route starts from air inlet 23, passes along air channel 26 and through flow restriction member 25*a*, then passes into the receptacle 24*a* and through the cartomizer channel 44*a* of the first cartomizer 4*a*, into the receptacle 32*a*, along the mouthpiece channel 33*a* of the mouthpiece part 3 to the opening 31*a*. Equally, a second route starts from air inlet 23, passes along air channel 26 and through flow restriction member 25*b*, then passes into the receptacle 24*b* and through the cartomizer channel 44*b* of the second cartomizer 4*b*, into the receptacle 32*b*, along the mouthpiece channel 33*b* of the mouthpiece part 3 and to the opening 31*b*. In this example, each of the first and second routes share a common component upstream of the flow restriction members 25 (namely, air channel 26 which is coupled to air inlet 23) but branch off from this common component. In the following, the cross-section of the routes is described as circular; however, it should be appreciated that the cross-section may be non-circular (e.g., any regular polygon) and also that the cross-section need not be a constant size or shape along the length of the two routes.

It should be appreciated by the foregoing that the example aerosol provision device 1 includes a number of components/parts that are duplicated and essentially provide separate and parallel air/aerosol flow paths through the device. Duplicated components are referenced by a number followed by a letter, e.g., 24*a*. Components indicated by the letter "a" are components that connect to, or define a first air/aerosol path, associated with a first cartomizer 4*a*, while components indicated by the letter "b" are components that connect to, or define a first air/aerosol path, associated with a second cartomizer 4*b*. Components having the same number will have the same functionality and construction as one another unless otherwise indicated. In general, the components will be collectively referred to in the following by their corresponding number, and unless otherwise indicated, the description applies to both components "a" and "b" referenced by that number.

In use, a user inhales on the mouthpiece part 3 of the example device 1 (and specifically through openings 31) to cause air to pass from outside the housing 20 of the reusable part 2, through the respective routes through the device along which the air/aerosol passes and ultimately into the user's mouth. The heating elements 43 are activated in order to vaporize the source liquid contained in the wicking elements 42 such that the air passing over/around the heating elements 43 collects or mixes with the vaporized source liquid to form the aerosol. Source liquid may pass into/along the wicking elements 42 from the liquid reservoir 41 through surface tension/capillary action.

Electrical power is supplied to the heating elements 43 from battery 21, controlled/regulated by control circuitry 22. The control circuitry 22 is configured to control the supply of electrical power from the battery 21 to the heating elements 43 in the respective cartomizers 4 so as to generate a vapor from the cartomizers 4 for inhalation by a user. Electrical power is supplied to the respective heating elements 43 via electrical contacts (not shown) established across the interface between the respective cartomizers 4 and the control part 2, for example through sprung/pogo pin connectors, or any other configuration of electrical contacts which engage when the cartomizers 4 are received in/connected to the receptacles 24 of the control part 2. Of course, respective heating elements 43 could be supplied with energy via other means, such as via induction heating, in which case electrical contacts that interfaces between the control part 2/receptacles 24 and the cartomizers 4 are not required.

The control circuitry 22 is suitably configured/programmed to provide functionality in accordance with embodiments of the disclosure as described herein, as well as for providing conventional operating functions of the aerosol provision device 1 in line with the established techniques for controlling conventional e-cigarettes. Thus the control circuitry 22 may be considered to logically comprise a number of different functional blocks, for example a functional block for controlling the supply of power from the battery 21 to the heating element 43a in the first cartomizer 4a, a functional block for controlling the supply of power from the battery 21 to the heating element 43b in the second cartomizer 4b, a functional block for controlling operational aspects of the device 1 in response to user input (e.g., for initiating power supply), for example configuration settings, as well as other functional blocks associated with the normal operation of electronic cigarettes and functionality in accordance with the principles described herein. It will be appreciated the functionality of these logical blocks may be provided in various different ways, for example using a single suitably programmed general purpose computer, or suitably configured application-specific integrated circuit(s)/circuitry. As will be appreciated the aerosol provision device 1 will in general comprise various other elements associated with its operating functionality, for example a port for charging the battery 21, such as a USB port, and these may be conventional and are not shown in the figures or discussed in detail in the interests of brevity.

Power may be supplied to the heating elements 43 on the basis of actuation of a button (or equivalent user actuation mechanism) provided on the surface of the housing 20 and which supplies power when the user presses the button. Alternatively, power may be supplied based on detection of a user inhalation, e.g., using an airflow sensor or pressure sensor, such as a diaphragm microphone, connected to and controlled by the control circuitry 22 which sends a signal to the control circuitry 22 when a change in pressure or airflow is detected. It should be understood that the principles of the mechanism for starting power delivery is not significant to the principles of the present disclosure.

As mentioned previously, an aspect of the present disclosure is an aerosol delivery device 1 configured to provide consistent aerosol delivery to the user regardless of the state/condition of the device 1. In the example aerosol delivery device 1 shown in FIGS. 1 and 2, the cartomizers 4 are provided separately from the control part 2 and the mouthpiece part 3 and can therefore be inserted into or removed from the receptacles 24. The cartomizers 4 may be replaced/removed for a variety of reasons. For example, the cartomizers 4 may be provided with different flavored source liquids and the user can insert two cartomizers 4 of different flavors (e.g., strawberry flavored and menthol/mint flavored) into the respective receptacles 24 to create different flavored aerosols, if desired. Alternatively, the cartomizers 4 can be removed/replaced in the event that a cartomizer 4 runs dry (that is, the source liquid in the liquid reservoir 41 is depleted).

Turning to the cartomizers 4 in more detail, the cartomizers 4 each comprise the housing 40, which in this example is formed of a plastics material. The housing 40 is generally in the form of a hollow tubular cylinder having an outer diameter and an inner diameter, with the walls of the inner diameter defining the limits of the cartomizer channel 44. The housing 40 supports other components of the cartomizer 4, such as the atomizer unit mentioned above, and also provides a mechanical interface with the receptacles 24 of the control part 2 (described in more detail below). In this example the cartridge has a length of around 1 to 1.5 cm, an outer diameter of 6 to 8 mm and an inner diameter of around 2 to 4 mm. However, it will be appreciated the specific geometry, and more generally the overall shapes involved, may be different in different implementations.

As mentioned, the cartomizer 4 comprises a source liquid reservoir 41 which takes the form of a cavity between the outer and inner walls of the housing 40. The source liquid reservoir 41 contains a source liquid. A source liquid for an electronic cigarette will typically comprise a base liquid formulation, which makes up the majority of the liquid, with additives for providing desired flavor/smell/nicotine delivery characteristics to the base liquid. For example, a typical base liquid may comprise a mixture of propylene glycol (PG) and vegetable glycerol (VG). The liquid reservoir 41 in this example comprises the majority of the interior volume of the cartomizer 4. The reservoir 41 may be formed in accordance with conventional techniques, for example comprising a molded plastics material.

The atomization unit of each cartomizer cartomiser 4 comprises heating elements 43 which in this example comprise an electrically resistive wire coiled around the respective wicking element 42. In this example, the heating elements 43 comprise a nickel chrome alloy (Cr20Ni80) wire and the wicking elements 42 comprise a glass fiber bundle, but it will be appreciated that the specific atomizer configuration is not significant to the principles described herein.

The receptacles 24 formed in the control part 2 are approximately cylindrical and generally have a shape (inner surface) that conforms to the outer shape of the cartomizers 4. As mentioned, the receptacles 24 are configured to receive at least a part of the cartomizers 4. The depth of the receptacles (that is a dimension along the longitudinal axis of the receptacles 24) is slightly less than the length of the cartomizers 4 (e.g., 0.8 to 1.3 cm) such that, when the cartomizers 4 are received in the receptacles 24, the exposed ends of the cartomizers 4 slightly protrude from the surface of the housing 20. The outer diameter of the cartomizers 4 is slightly smaller (e.g., about 1 mm or less) than the diameter of the receptacles 24 to allow the cartomizers 4 to slide into the receptacles with relative ease, but to fit reasonably well within the receptacles 24 to reduce or prevent movement in a direction orthogonal to the longitudinal axis of the cartomizer 4. In this example the cartomizers 4 are mounted in a generally side-by-side configuration in the body of the control part 2.

In order to insert, replace or remove the cartomizers 4, the user will typically disassemble the device 1 (e.g., into a state generally as shown in FIG. 2). The user will remove the mouthpiece part 3 from the control part 2 by pulling the mouthpiece part 3 in a direction away from the control part 2, remove any previous cartomizers 4 located in the receptacles (if applicable) by pulling the cartomizers 4 in a direction away from the control part 2, and insert a new cartomizer 4 in the receptacle 24. With the cartomizer(s) 4 inserted in the receptacles 24, the user then reassembles the device 1 by coupling the mouthpiece part 3 to the reusable part 2. An assembled device 1 is schematically shown in FIG. 1, although it should be noted that certain features are not shown to scale and exaggerated for the purposes of clarity, such as the gap between the mouthpiece part 2 and the housing 20 of the control part 2, for example.

As described the control part 2 is provided with flow restriction members 25 located in respective flow paths for the separate cartomizers 4. In this example, each flow path is provided with a single flow restriction member 25, disposed at the upstream side of the receptacles 24. The flow restriction members 25 in this example are mechanical one-way valves 25, comprising a plurality of flaps formed of an elastomeric material; however, it will be appreciated that any suitable valve is considered within the scope of the present disclosure. The flaps of this example are biased to a closed position and, in this position, prevent or at least obstruct air passing from the airflow path 26 into the receptacles 24. The elastomeric flaps may be fixed on one side to the outer wall of the flow paths (or to a suitable valve housing that is subsequently fixed to the outer wall of the flow paths) and are free to move at the other end. The elastomeric flaps are arranged to open in response to a force applied to the flaps in a certain direction (in this example, in a downward direction from the receptacles towards the valves).

Figure 3A:
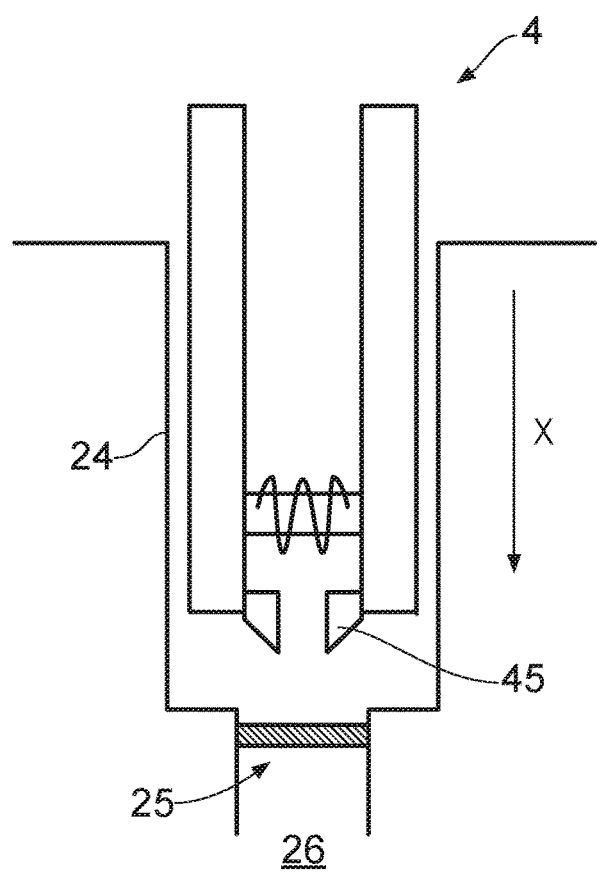
FIG. 3a schematically shows a cartomizer of FIGS. 1 and 2 in a semi-inserted state into a receptacle of the control part of the aerosol delivery system of FIGS. 1 and 2.
Figure 3B:
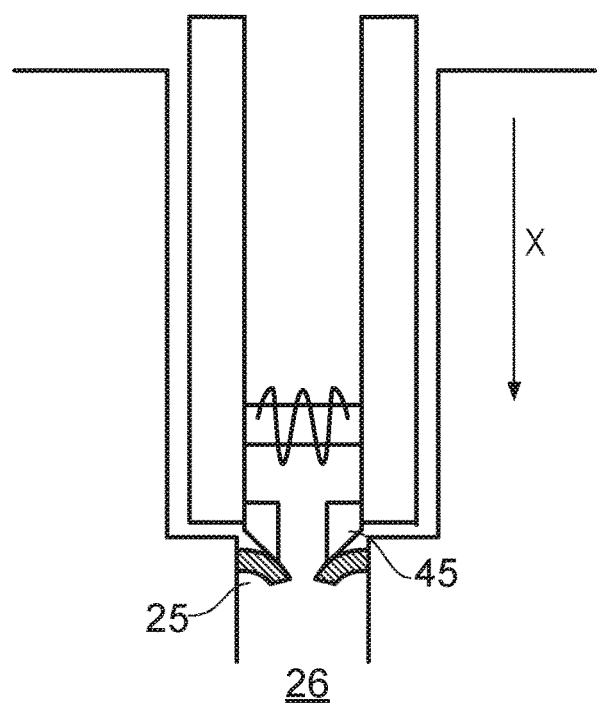
FIG. 3b schematically shows the cartomizer of FIG. 3a in a fully inserted state into the receptacle of the control part of the aerosol delivery system of FIGS. 1 and 2.

FIGS. 3a and 3b show an example of the valve operation according to the present example. Each of the cartomizers 4 is fitted with a mechanical engagement member arranged to mechanically engage with the respective valve 25. In the example shown in FIGS. 3a and 3b, the mechanical engagement member is a protrusion 45 (not shown in FIGS. 1 and 2 for clarity) that extends beyond the circular base of the cartomizer 4. The protrusion 45 in this example takes the shape of an annular ring or a hollow truncated cone which tapers in a direction away from the cartomizer 4; that is, the tapered portion extends downwardly beyond the base of the housing 40. The protrusion shown in FIGS. 3a and 3b is attached to the inner wall of the cartomizer 4 using appropriate bonding techniques, e.g., adhesive, and also extends partway into the cartomizer channel 44 causing a narrowing of the cartomizer channel 44. However, it should be appreciated that other shapes and arrangements of the mechanical engagement member are considered within the scope of the present disclosure. Generally, the shape of the protrusions 45 will be dependent upon the configuration/size of the valve 25, receptacles 24, and cartomizer 4. The protrusion 45 may also be integrally formed with the housing 40 of cartomizer 4 as opposed to a separate component that is attached to the housing.

With reference to FIG. 3a, a user may push the cartomizer 4 into the receptacle 24, e.g., by applying a force to the cartomizer 4 along the direction indicated by arrow X or by allowing the cartomizer 4 to drop into the receptacle 24 under the force of gravity. In FIG. 3a the cartomizer 4 is only partially inserted into the receptacle 24 and protrusion 45 is not in contact with the valve 25. Accordingly, in this arrangement, the valve 25 is biased closed and no (or little) air can flow through valve 25.

By applying additional force (or simply allowing the cartomizer to be completely received in the receptacle), the protrusion 45 contacts the valve 25 causing the valve 25 to open. More specifically, the tapered portions of the protrusion 45 cause the free ends of the elastomeric flaps to bend/angle downwards relative to their fixed position on the outer wall of the airflow paths 26. This bending causes the free ends of the elastomeric flaps to separate from one another and form a gap through the valve 25, through which air from the airflow path 26 may flow and into the cartomizer channel 44 of the cartomizer 4. Should the user then remove the cartomizer 4 from the receptacle at a later time, the elastomeric flaps return to their biased, closed position as the protrusion 45 is moved away from the flaps of valve 25.

In this example aerosol provision device 1, the cartomizers 4 are freely inserted into the receptacles. To ensure that both the valve 25 is opened correctly/fully and that there is sufficient electrical contact between the electrical contacts (not shown) of the cartomizer 4 (which are electrically connected to the heating elements 43) and receptacles 24 (which are electrically connected to power supply 21), the exposed end of the cartomizer 4 can be contacted by receptacle 32 of the mouthpiece part 3 when the mouthpiece part 3 is coupled to the control part 2. The receptacles 32 are formed in a similar manner to receptacles 24 in that they are cylindrical recesses within mouthpiece part 3 sized to receive a part of the cartomizers 4. The distance between the bottom surface of the receptacle 24 and the top surface of receptacle 32 when the mouthpiece part 3 and control part 2 are coupled is set to be equal to or slightly less (e.g., 0.5 mm) than the length of the cartomizers 4. In this way, when the user applies the mouthpiece part 3 after inserting the cartomizer(s) 4 into receptacle(s) 24, the receptacle 32 contacts the exposed end of the cartomizer 4 and forces the cartomizer 4 to be seated properly in receptacle 24 as the user applies a force to the mouthpiece part 3. When the mouthpiece part 3 is coupled to the control part 2, the cartomizer 4 is restricted from moving in the longitudinal direction meaning that good electrical contact and good contact with the valve can be ensured. In other words, the cartomizers 4 are clamped in place within the receptacles 24 and 32 of the device 1 when the lid is coupled to the control part 2. This configuration may also be applied when the cartomizers 4 are mechanically connected to the receptacles 24, e.g., via a press-fit mechanism.

In addition, sealing can be provided between the cartomizer channel 44, mouthpiece channel 33 and airflow path 26 meaning that leakage of the air/aerosol into other parts of the device 1 can be reduced. To help improve this sealing, a seal (such as an elastomeric O-ring or equivalent) can be placed so as to surround the entrances to cartomizer channel 44, mouthpiece channel 33 and air channel 26.

As should be appreciated from the above, when a cartomizer 4 is inserted into a respective receptacle 24, the corresponding flow restriction member 25 is open which connects the respective first or second flow path to the common air channel 26. Conversely, when a cartomizer 4 is not located in the respective receptacle 24, the flow restriction member 25 is closed which isolates the first or second aerosol pathway from the common air channel 26, essentially meaning that no air flows along this path. Accordingly, regardless of the state/configuration of the aerosol provision device 1 (e.g., in this example, whether both or only one of the cartomizers 4 are present) the user is provided with a more consistent experience/aerosol delivery.

Aerosol is defined as the suspension of solid or liquid particles in air or another gas, and as a result one can define a certain concentration of source liquid particles to air. The rate at which vaporization occurs depends on many factors, such as the temperature of the heater (or power supplied to the heater), the airflow rate through the cartomizer 4, the wicking rate of liquid wicking to the heater along wicking element 42, etc. By way of illustration only, suppose for a given inhalation strength, the device of FIG. 1 (when both cartomizers 4a and 4b are inserted in the receptacles 24a and 24b) enables aerosol to be inhaled by the user having about 10% of the aerosol composed of vaporized liquid particles.

For the purposes of the example, it is assumed here that around half of the vaporized liquid particles (i.e., 5%) is produced by each of the cartomizers 4a and 4b.

Now we consider two situations where only one cartomizer 4a is present in the device 1. In one situation, cartomizer 4a is present and valve 25b (i.e., the valve associated with cartomizer 4b) is open. This allows air to flow both through cartomizer 4a and through receptacle 24b (which does not include cartomizer 4b). We assume for the sake of simplicity that this would mean 50% of the air flows through cartomizer 4a and 50% flows through receptacle 24b. Cartomizer Cartomiser 4a does not experience any change in the various conditions (e.g., air flow rate, wicking rate, etc.) as compared to the situation when both cartomizers 4a and 4b are present. Accordingly, the aerosol inhaled by the user is made up of only 5% vaporized liquid particles. In other words, the concentration of liquid source particles in the inhaled air has decreased compared to the situation where both cartomizers 4a and 4b are present. This has an impact on the user's perception of the inhaled aerosol (e.g., the taste/flavor may not be as strong or noticeable).

The other situation is where cartomizer 4a is present but valve 25b (i.e., the valve associated with cartomizer 4b) is closed. This is in accordance with the teachings of the present disclosure. This situation allows air to flow through cartomizer 4a but not through receptacle 24b. We assume for the sake of simplicity that this would mean 100% of the air flows through cartomizer 4a. In this situation, cartomizer 4a does experience a change in the various conditions associated with vaporization. In this case, the airflow rate increases through cartomizer 4a which is likely to draw more liquid along the wicking element 42a and thus cause more vaporization of the source liquid. It should be noted that an increased airflow rate also has an increased cooling effect on the heating element 43a, but in some implementations the heating elements 43 can be controlled to maintain the heating elements 43 at a certain temperature (e.g., by increasing the power supplied to the heating element 43). Accordingly, the concentration of source liquid to air is increased in this scenario relative to the situation where valve 25b is open. In other words, the concentration of air to vaporized liquid particles in the situation where valve 25b is closed is closer to (and in some implementations be equal to) the concentration of air to vaporized liquid particles in the situation where two cartomizers 4a and 4b are present (e.g., this may result in aerosol inhaled by the user made up of between 6% to 10% vaporized liquid particles).

Accordingly, the user is presented with less of a discrepancy between the aerosol they receive regardless of whether one cartomizer or both cartomizers 4 are present in the device. In some cases, the flavor or mix of flavors will change (e.g., when using cartomizers containing different flavored source liquids) but the user is provided with a generally consistent volume/quantity of vaporized liquid particles in either situation. This generally improves the user experience of the device and means that a user is able to use the device more flexibly (i.e., using one or two cartomizers) and receive a consistent experience.

In the above described implementation, the flow restriction members 25 are either controlled to be fully open when the cartomizer 4 is present in the receptacle 24, or fully closed when the cartomizer 4 is not present in the receptacle 25. However, in other implementations, the flow restriction members 25 are able to be actuated to varying positions between an open and closed position. That is, the flow restriction member 25 can be half open, one quarter open, etc. The extent to which the flow restriction member is open alters the resistance to draw of the device 1 (that is the resistance the user feels when sucking on the mouthpiece 3 of the device)—for example, a flow restriction member 25 that is half open has a greater resistance to draw on than a flow restriction member 25 that is fully open.

In other implementations, the flow restriction members 25 may be electrically operated valves, for example having an electric motor or the like which is driven in response to a signal to open the valve. That is, the control circuitry 22 in some implementations is arranged to actuate the electrically operated flow restriction members 25 in response to a certain input. The certain input in this implementation is not an input by the user, but is instead an input that is dependent upon the current state/configuration of the aerosol provision device 1. For example, when each cartomizer 4 is inserted into the receptacle 24, an electrical connection is made between the electrical contacts (not shown) on the cartomizers 4 (that connect to the heating element 43) and the electrical contacts in the receptacle (that connect to the control circuitry 22). The control circuitry 22 in such implementations is configured to detect a change in the electrical properties when the cartomizer 4 is received in the receptacle (e.g., by detecting a change in resistance). This change in the electrical property is indicative of a cartomizer 4 being present in the receptacle 24 and upon detecting the change in electrical property, the control circuitry 22 is configured to transmit a signal to the electrically operated flow restriction member 25 (e.g., by supplying an electrical power from the battery 21 to a motor of the flow restriction members 25) to cause the flow restriction member 25 to open. That is, the control circuitry 22 can be configured to detect the presence of the cartomizers 4 and is arrange to open the flow restriction member 25 if the cartomizer 4 is present within receptacle 24 or close the flow restriction members 25 if the cartomizer 4 is not present within the receptacle. It should also be appreciated that in the same way as the mechanical implementations described above, the electrically operated flow restriction members can be configured to be in an open, closed, or partially open state.

In other implementations, the consistency of aerosol delivery regardless of the state of the aerosol provision device 1 may not be the primary focus. Alternatively, the flow restriction members 25 may be used to control the relative proportions of aerosol generated by each of the two cartomizers 4.

For instance, in an implementation in which mechanically actuated flow restriction members 25 are provided, the cartomizers 4 are provided with different shaped protrusions 45 which open or close the flow restriction members 25 to varying degrees. In this case, different source liquids may be provided in cartomizers having different shaped protrusions 45. For example, although not shown, the tapered portion on protrusion 45 of cartomizer 4a may be shorter than that shown in FIGS. 3a and 3b (and thus also have a greater taper angle), while the tapered portion of protrusion 45 of cartomizer 4b may be longer than that shown (and thus have a smaller taper angle). The shorter protrusion 45 of cartomizer 4a penetrates less deeply into the flow restriction member 25 meaning the flow restriction member 25 is only opened by a small amount (say, 25% open). The longer protrusion of cartomizer 4b penetrates deeper into the flow restriction member 25 causing the flow restriction member 25 to open by a larger amount (say, 75% open). In this situation, as the user inhales on the device, roughly 25% of the air will pass through cartomizer 4a and 75% of the air will pass through cartomizer 4b. This means the aerosol inhaled by the user will comprise a greater volume of liquid vapor generated by cartomizer 4b compared to the volume of the liquid vapor generated by cartomizer 4a. Assuming cartomizer 4a comprises a cherry flavored source liquid and cartomizer 4b comprises a strawberry flavored source liquid, the user will receive an aerosol comprising more strawberry flavor than cherry flavor, in this particular example.

It should also be appreciated that this form of control of the proportions of aerosol generated from each cartomizer 4 may also be applied to electrically operated flow restriction members 25. For example, each cartomizer 4 may be provided with a computer readable chip that includes information about the source liquid contained in the cartomizer 4 (e.g., a flavor or strength of nicotine, for example). The control circuitry 22 can be provided with (or connected to) a mechanism for reading the chip of the cartomizer 4 to identify a property of the source liquid contained in the reservoir 41. As a result, the control circuitry 22 actuates the flow restriction members 25 to open to a certain degree based on the type of source liquid and accordingly configures different proportions of the air/aerosol to be provided to the user. For instance, in line with the above example, the flow restriction member 25a may be set to be 75% open while the flow restriction member 25b may be set to be 25% open. Here it should also be noted that an electrical based system offers improved flexibility over the mechanical system in that the control circuitry 22 can set the proportions of the aerosol relative to the source liquids within the device—that is, the device could be set to provide an aerosol comprising more strawberry flavor than cherry flavor, or more cherry flavor to apple flavor, based on a look-up table or the like.

In addition to the above, the flow restriction members 25 may be actuated based on the amount of source liquid contained in the cartomizers 4. For example, if cartomizer 4a contains a greater volume of source liquid in the liquid reservoir 41a than cartomizer 4b, the flow restriction member 25a may be opened by a greater amount than flow restriction member 25b. In this way, as a user inhales aerosol, the aerosol contains a greater proportion of vaporized source liquid from cartomizer 4a than from cartomizer 4b. This may be useful to help reduce the likelihood of one cartomizer (e.g., cartomizer 4b) "drying out" (i.e., using up its source liquid) before the other cartomizer (e.g., cartomizer 4a). Providing this arrangement may ensure that the user does not experience an unpleasant taste when, for example, one of the cartomizers 4 dries out and starts heating a dry wicking element 42.

In system in which electrically operated flow restriction members 25 are provided, the aerosol provision device 1 is provided with some mechanism for sensing/determining the quantity of aerosol contained in each of the cartomizers 4. For example, the walls of the cartomizer housing 40 or the walls of the receptacles 24 may be provided with separate electrically conductive plates arranged to face one another such that the volume of source liquid in the cartomizer 4 is situated between the plates when the device 1 is in the assembled state. The plates are arranged to be electrically charged (e.g., via power supplied from battery 21 either continuously or intermittently) and the control circuitry 22 is configured to determine a capacitance measurement of the plates. As the volume of liquid located between the plates changes, the capacitance value changes and the control circuitry 22 is configured to identify this change and determine the quantity of liquid remaining. The above is just one example of how a quantity of source liquid in the reservoir 41 of the cartomizers 4 can be detected, but the principles of the present disclosure are not limited to this technique. Once the control circuitry 22 identifies the quantity of liquid remaining, the control circuitry 22 actuates the flow restriction members 25 as described above. This may include actuating the flow restriction members 25 to different positions between an open and closed position based on the quantity aerosol precursor material remaining in the two cartomizers 4 (or more generally in the aerosol generating areas) to vary the ratio of aerosols generated from the two cartomizers 4. Additionally or alternatively, the flow restriction members 25 may be configured to remain open when a quantity of aerosol precursor is detected in the cartomizer (or more generally in the aerosol generating areas) and to close when the quantity falls below a certain limit (e.g., below 0.1 ml) or when it is detected that no aerosol precursor material remains.

In a system in which mechanically operated flow restriction members 25 are provided, the aerosol provision device 1 may include flow restriction members 25 that are activated in proportion to the weight of the cartomizers 4. In other words, and with reference to FIGS. 3a and 3b, a heavier cartomizer (i.e., one containing more source liquid) applies a greater downward force to the flow restriction member 25 than a lighter cartomizer (i.e., one containing less source liquid). This means the valves 25 open or close to a greater or lesser extent based on the weight of the cartomizers 4 and, accordingly, provide different proportions of aerosol from each of the cartomizers as the user inhales.

Hence it has been described above that the flow restriction members 25 are configured to vary the airflow through the respective cartomizers based on the presence of the cartomizers in the system and/or a parameter associated with the cartomizers in the system (e.g., a type of the source liquid or the quantity of source liquid in the cartomizer).

It should be appreciated that while the above techniques of controlling the flow restriction members 25 on the basis of a property of the cartomizer 4 have been described in isolation, it should be appreciated that in other implementations a combination of these techniques may equally be applied. For example, the percentage of airflow through cartomizer 4a may be set to be higher than the percentage of airflow through cartomizer 4b based on a type of liquid, but the percentages may also be weighted based on the quantity of liquid in the cartomizers 4. For instance, suppose the split is 75% to 25% based on the liquid type, however the split might be controlled to be 60% to 40% based additionally on the liquid level.

It should also be appreciated that while the above describes implementations where the flow restriction members 25 are located at the entrances to the receptacles 25, it should be appreciated that the flow restriction members 25 can be located at other positions along the separate flow paths within the device 1. In other words, the flow restriction members 25 may be disposed at any position along the separate flow paths for air or aerosol through the device. For example, the flow restriction members may be located in receptacles 32 or mouthpiece channels 33 within the mouthpiece part 3—that is, downstream of the atomization units of the cartomizers 4. However, the flow restriction members are not provided at locations that are common to the separate flow paths through the device. For instance, a flow restriction member 25 is not provided at the air inlet 23 of the device shown in FIG. 1 or 2. In the described implementations, the flow restriction member 25 is provided at a location at which the flow of air through one respective cartomizer is altered. It should also be appreciated that multiple flow restriction members 25 may be provided for each flow path—for example, flow restriction members 25 may be placed before air enters the cartomizer channel 44 (e.g., in the entrance to receptacle 24 as shown in FIGS. 1 and 2) and also after aerosol exits cartomizer channel 44 (e.g., in the exit from receptacle 32 in mouthpiece channel 33). This can provide the advantage of redundancy should one of the flow restriction members fail and/or permits the use of less robust or cheaper flow restriction members within the device 1.

Figure 4A:
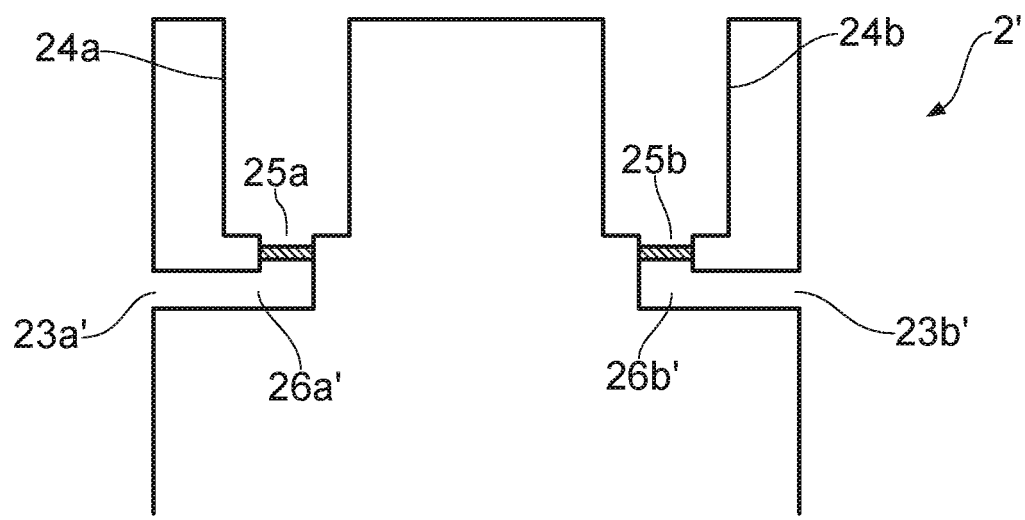
FIG. 4a schematically shows, in cross-section, an alternative control part in which each receptacle is provided with an individual air flow path connected to an individual air inlet.
Figure 4B:
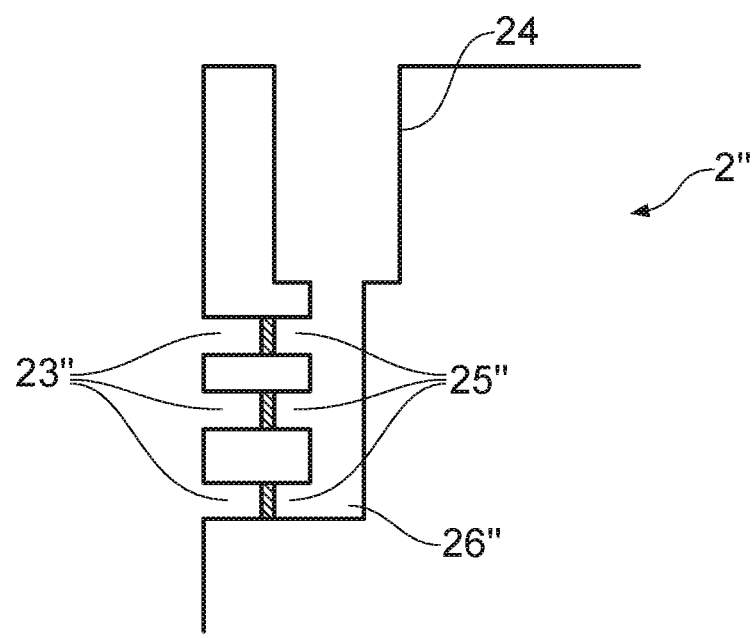
FIG. 4b schematically shows, in cross-section, yet another alternative control part in which each receptacle is provided with an individual air flow path connected to multiple air inlets, each air inlet having a flow restriction member.

FIGS. 4a and 4b schematically show, in cross-section, alternative arrangements of flow restriction members and control parts. FIG. 4a depicts a control part 2' which is the same as control part 2, with the exception that control part 2' comprises two air inlets 23a' and 23b' and two air channels 26a' and 26b'. As can be seen from FIG. 4a, the air channels 26' are separate from one another—that is, they are not fluidly connected within the control part 2'. Each air channel 26' connects to a receptacle 24 and to an air inlet 23'. In essence, FIG. 4a depicts an implementation that is identical to the implementations described above with respect to FIGS. 1 and 2 with the exception that there is no shared (or common) component of the flow paths through the device. That is, air channel 26a' connects air inlet 23a' to receptacle 24a only, and air channel 26b' connects air inlet 23b' to receptacle 24b only.

FIG. 4b depicts an example control unit 2'' which is the same as control unit 2 with the exception that there are multiple air inlets 23'' (specifically three) connected to a single receptacle 24 by an air channel 26''. FIG. 4b only depicts half the control unit 2'' (specifically the left-half with respect to FIGS. 1 and 2), although it should be appreciated there is a corresponding arrangement on the right-half of the control unit 2''. In the implementation of FIG. 4b, three flow restriction members 25'' are provided between each of the three air inlets 23'' in the control part 2''. In this implementation, each of the three air inlets 23'' can be controlled to be in an open or closed state. In this case, the resistance to draw can be changed depending on how many of the flow restriction members 25'' are open. For example, when all three flow restriction members 25'' are open, the resistance to draw is relatively low compared to the case when only one of the three flow restriction members 25'' are open. Accordingly, by altering the resistance to draw, the device 1 can alter the relative percentage of the total air inhaled that passes through each cartomizer 4, in a similar manner to that described above. For example, if the flow restriction members 25'' that allow air to pass through cartomizer 4a are set to all be fully open, whereas the flow restriction members 25'' that allow air to pass through cartomizer 4b are set so that only one of the three are open, as the user inhales on the device, a greater proportion of the inhaled air passes through cartomizer 4a compared to cartomizer 4b as the flow path through cartomizer 4b has a greater resistance to draw.

In this arrangement shown in FIG. 4b, the flow restriction members 25'' may be electrically actuated or mechanically actuated, depending on the application at hand. That is, the flow restriction members 25'' may automatically open or close in response to a mechanical or electrical input. Moreover, in some implementations, the user may be provided with the option to manually control which of the flow restriction members 25'' are open or closed, depending on the user's preference.

As should be appreciated by the above, in use, airflow through the aerosol provision system can be controlled on the basis of a number of parameters. However, more generally, when using the device a first flow restriction member is adjusted in order to vary the flow of air along a first flow pathway arranged to pass through a first aerosol generating area and fluidly connected to the mouthpiece and a second flow restriction member is adjusted in order to vary the flow of air along a second flow pathway arranged to pass through a second aerosol generating area and fluidly connected to the mouthpiece. As described above, the flow restriction members vary the flow of air along respective pathways based on the presence of an aerosol generating component in the respective aerosol generating areas in the system and/or a parameter associated with the respective aerosol generating component in the system.

In addition, or as an alternative to controlling airflow through the device 1, aspects of the present disclosure relate to the distribution of power between the cartomizers 4a and 4b in order to influence aerosol generation.

As mentioned, the control circuitry 22 is configured to control the supply of power to the heating elements 43 of the different cartomizers 4; hence one function of the control circuitry 22 is power distribution. As used herein the term "power distribution circuitry" refers to the power distribution function/functionality of the control circuitry 22.

In one implementation, power is distributed on the basis of the presence or absence of aerosol generating components, e.g. the cartomizers 4, in the respective aerosol generating areas, e.g. receptacles 24. In much the same way as described above, the control circuitry 22 can be configured to electrically detect whether a cartomizer 4 is installed in each of the receptacles 24—for example, the control circuitry 22 may be configured to detect a change in electrical resistance as the cartomizer 4 is inserted into the receptacle 24 and an electrical connection is established between the heating wire 43 and the control circuitry 22 (e.g., through the coupling of electrical contacts on the cartomizers and the receptacles). The control circuitry 22 is therefore configured to identify how many cartomizers 4 are installed within the device at any one time, in this case by detecting a change in an electrical property (e.g. resistance) of the circuitry within the device 1. As mentioned above, when the aerosol generating component is an aerosol precursor material, e.g. a liquid, capacitance is a suitable way of detecting whether an aerosol generating component is present in the aerosol generating area, although other detection mechanisms may be suitable, e.g., optical.

Figure 5A:
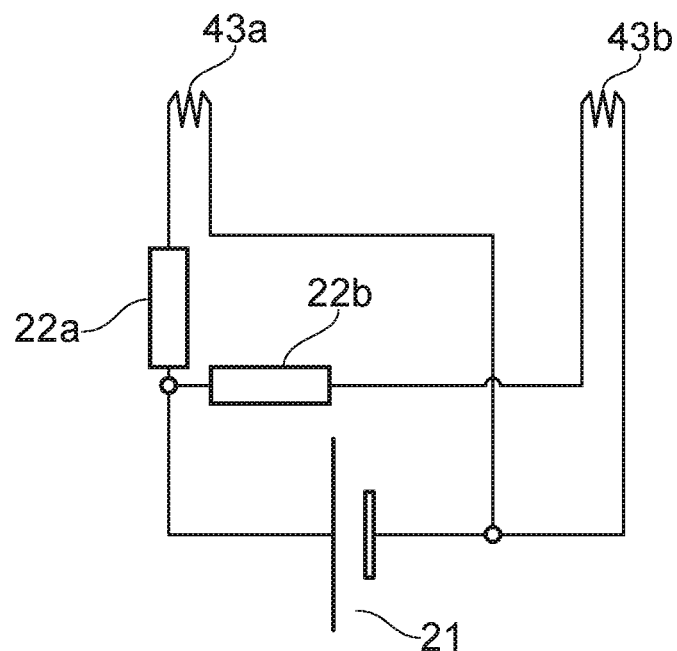
FIG. 5a diagrammatically shows an example circuit layout in a state where two cartomizers (and two heating elements) are electrically connected to the control part of FIGS. 1 and 2.

FIG. 5a is an exemplary schematic circuit diagram showing the electrical connections between battery 21 and the heating wires 43a and 43b of two cartomizers 4a and 4b installed in the device 1. FIG. 5a shows heating wire 43a and heating wire 43b connected in parallel with the battery 21. In addition, each arm of the parallel circuit is provided with a schematic representation of functional blocks of the control circuitry 22, referred to here as control circuitry block 22a and/or 22b. It should be appreciated for simplicity that the functional blocks of control circuitry 22 are shown individually for ease of visualization; however, the control circuitry 22 may be a single chip/electronic component configured to perform the described functionality, or each functional block may be implemented by a dedicated ship/circuit board (as generally described above). Control circuitry block 22a is a power control mechanism for controlling the power supplied to heating wire 43a, and control circuitry block 22b is a power control mechanism for controlling the power supplied to heating wire 43b. The power control mechanism may implement, for example, a pulse width modulation (PWM) control technique for supplying power to the respective heating wires 43.

In FIG. 5a, two cartomizers 4 are installed in the device as identified by the presence of two heating wires 43 in FIG. 5a. The control circuitry 22 is configured to identify the presence of both cartomizers 4 in the device and subsequently supply power to both cartomizers 4. Assuming the battery voltage is around 5 volts, each heating wire 43a may be supplied with an (average) voltage around 2.5 volts. For the sake of simplicity, we assume here that each heating wire 43 is identical and, as a result, when power is supplied to each heating wire and vaporization of the source liquid occurs, each cartomizer 4 produces the same quantity/volume of vapor.

Figure 5B:
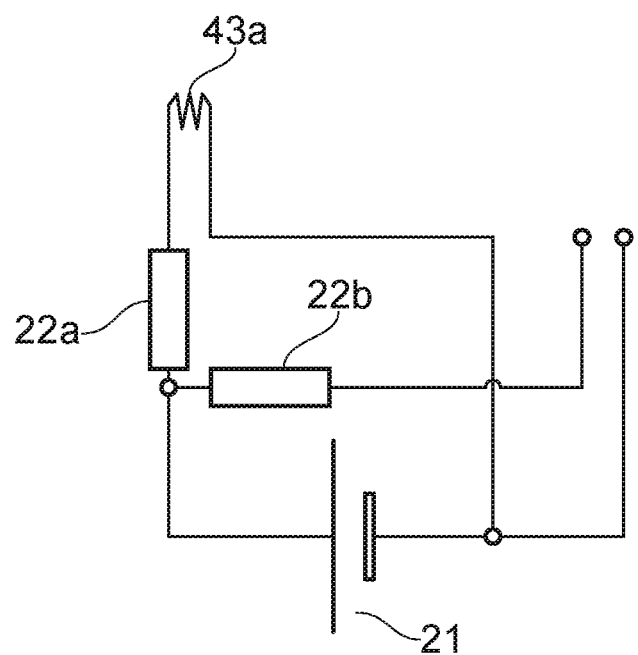
FIG. 5b diagrammatically shows the example circuit layout of FIG. 5a in a state where only one cartomizer (and one heating element) is electrically connected to the control part of FIGS. 1 and 2.

FIG. 5b schematically represents the same circuitry as in FIG. 5a; however the second cartomizer 4b has been removed from the circuitry/device, meaning that heating wire 43b is no longer connected to the circuitry. In this case, and assuming circuitry 22a operates in the same way, heating wire 43a produces approximately the same quantity of vapor as in the case where cartomizer 4b is present as the power supplied to the heating wire is constant, however the total quantity of vapor produced by the device 1 as a whole is less because the contribution from cartomizer 4b is no longer present.

To compensate for this, circuitry 22a is configured to increase the voltage/power supplied to the heating wire 43a, e.g., by increasing the voltage supplied from 2.5 volts to 3.5 volts. For example, supposing the electrical resistance of the heating wires 43a and 43b are the same, when one cartomizer is removed from the circuit, the power P supplied to the remaining cartomizer can be doubled by supplying $\sqrt{2}$ times the voltage before. In simplistic terms, doubling the power supplied to a heating wire may cause approximately twice the volume of vapor to be produced.

That is, in the absence of one cartomizer in the device, the power supplied to the remaining cartomizer is increased in order to generate more vapor from the cartomizer that is present in the device. Accordingly, the heating wire 43a is capable of generating a greater quantity of vapor to compensate for the quantity of vapor that would otherwise be supplied from cartomizer 4b. In this case, the total quantity of vapor produced per inhalation can be controlled to be approximately the same (if not the same) regardless of whether the user installs one or two cartomizers 4 in the device 1. In this way, the user is provided with a consistent volume of vapor whether one or two cartomizers are installed in the device, and therefore an overall more consistent experience when using the device 1.

In practice, there are likely to be other effects (such as heat transfer efficiency to the liquid in the wicking material 42, the rate of liquid wicking, etc.) that means the volume of aerosol might not be quite double when doubling the power. However, the device of the present disclosure can be calibrated such that the power supplied to the heating elements 43 is chosen such that twice the volume of vapor is generated from a single cartomizer 4 when only one cartomizer is present in the device.

It should also be appreciated that in some implementations the quantity of vapor inhaled may not necessarily be doubled to give a consistent user experience. For example, it may be determined that the user only requires around 80% or 90% or 95% of the total volume of vapor generated with two cartomizers to be generated when one cartomizer is installed in the device. That is, the difference in the volume of aerosol produced in the situation where only one cartomizer is present in the device is less than or equal to 20%, or 10%, or 5%. This may be down to the volume of air that can be inhaled through a single cartomizer 4/flow path (i.e., due to an increase in resistance to draw).

In other implementations, it should be appreciated that control circuitry 22 may distribute power between the cartomizers 4 according to certain properties of the cartomizer, e.g., the liquid stored within the liquid reservoir 41 of the cartomizers. For instance, cartomizer 4a may contain a strawberry flavored source liquid, while cartomizer 4b may comprise a cherry flavored source liquid. When both cartomizers 4 are installed in the device 1, the control circuitry 22a may distribute the power such that 30% of the supplied power is directed to cartomizer 4a and 70% of the supplied power is directed to cartomizer 4b. In such a situation, the inhaled aerosol comprises a larger proportion of cherry flavored aerosol compared to strawberry flavored aerosol. However, should cartomizer 4b be removed, the power distributed to cartomizer 4a is increased by more than double to provide the same quantity of vaporized liquid.

The circuitry blocks 22a and 22b are configured above to supply power to the heating wires 43 using a PWM technique. PWM is a technique that involves pulsing a voltage on/off for in predetermined times. One on/off cycle includes a duration of the voltage pulse and the time between subsequent voltage pulses. The ratio between the duration of a pulse to the time between pulses is known as the duty cycle. In order to increase (or decrease) the voltage (and hence power) supplied to the heating wires 43, the circuitry blocks 22a and 22b are configured to vary the duty cycle. For example, to increase the average voltage supplied to the first heating wire 43a, the duty cycle can be increased from 50% (that is in one cycle, for half the cycle a voltage is supplied to the heating wire and for the other half a voltage is not supplied to the heating wire). The average voltage is a measure of the voltage supplied over the period of the duty cycle. In other words, each voltage pulse may have an amplitude equal to the battery voltage, e.g., 5 V, but the average voltage supplied to the heating wire 43 is equal to the battery voltage supplied multiplied by the duty cycle.

Figure 6A:
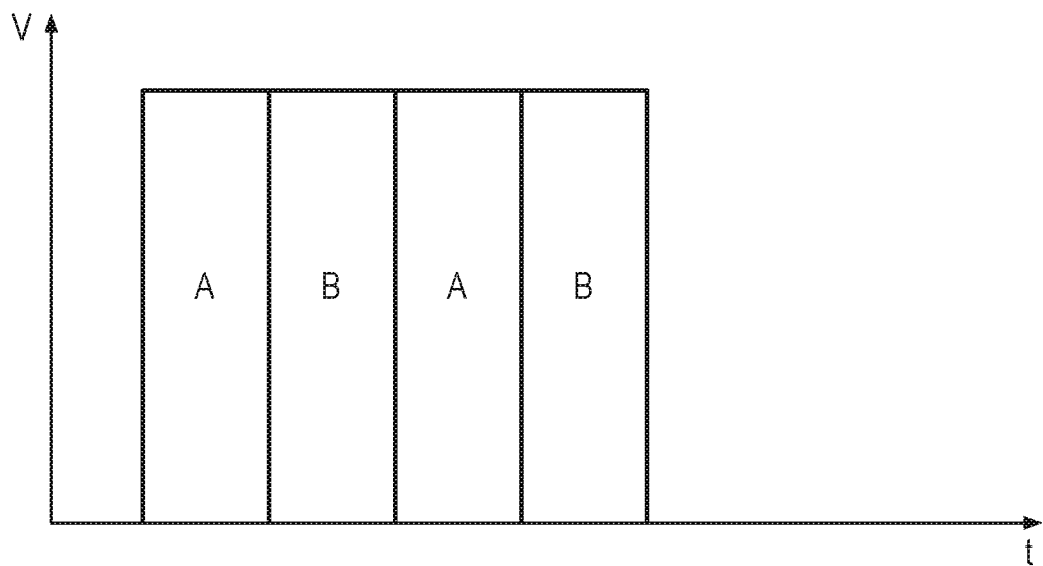
FIG. 6a depicts a graph of voltage versus time illustrating a duty cycle of 50% for voltage pulses supplied to heating elements of a first cartomizer, cartomizer A, and a second cartomizer, cartomizer B.
Figure 6B:
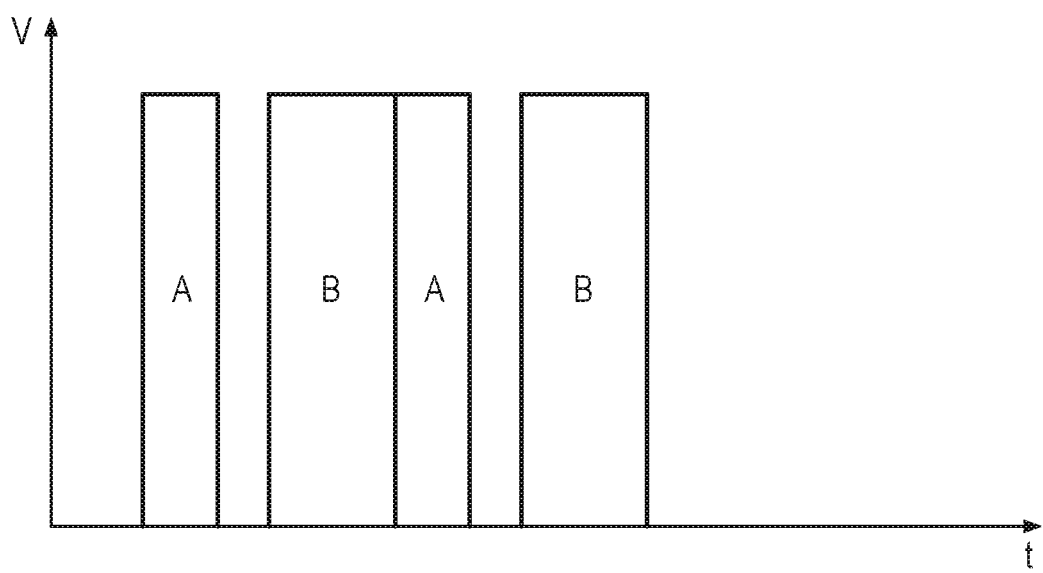
FIG. 6b depicts a graph of voltage versus time illustrating a duty cycle of 50% for voltage pulses supplied to heating elements of cartomizer B and a duty cycle of around 30% for voltage pulses supplied to heating elements of cartomizer A.

FIGS. 6a and 6b are graphs showing example PWM power distributions. Along the x-axis is indicated time and along the y-axis is indicated voltage (i.e., the voltage value of the various voltage pulses). In FIGS. 6a and 6b, pulses labelled "A" indicate a voltage supplied to heating wire 43a, while pulses labelled "B" indicate a voltage supplied to heating wire 43b.

FIG. 6a shows a first example power distribution in which an equal average voltage is supplied to each of the heating wires 43. As mentioned, a cycle is the total time from the start of a pulse to the start of the next pulse, and in this example, for both heating wires 43a and 43b, half of the total time is spent supplying a voltage pulse to the heating wire—hence, the duty cycle for each heating wire is 50%. In FIG. 6b, the duty cycle for pulse A is reduced to around 30%, meaning that a larger average voltage is supplied to heating wire 43b relative to heating wire 43a resulting a greater volume of source liquid being vaporized from cartomizer 4b.

It should also be appreciated from FIGS. 6a and 6b that the voltage pulses are alternately applied to heating wires 43a and 43b—that is, the voltage pulses supplied to heating wire 43a are not in phase. This can lead to a simpler control mechanism being implemented in control circuitry 22. For example, a single switch configured to switch between a "connected to heating wire 43a" state, a "connected to heating wire 43b" state, and a "not connected" state can be implemented in control circuitry 22 to realize the three possible connection states. In FIG. 6a, the switch can be controlled to alternate between the two connection states, while in FIG. 6b the switch can be controlled to also pass through the not connected state (i.e., in order to realize the gap between pulses A and B in FIG. 6b). In this way the control circuitry and method of controlling the circuitry can be simplified. However, it should be appreciated in other implementations that different control mechanisms may be used, e.g., each heating wire 43 can be controlled by a separate switch.

It should also be appreciated that although it is shown in FIGS. 6a and 6b that each heating wire is alternatively supplied with a voltage pulse, the period of one cycle may be a few tens of ms, meaning that in practice each cartomizer 4a and 4b generates vapor at approximately the same time and thus both generated vapors are delivered to the user and substantially the same time.

As mentioned above, it should also be appreciated that the total power supplied to the heating elements 43 may be dependent upon the strength of a user inhalation. That is, if a user inhales more strongly, a greater voltage may be supplied to the heating elements 43 to generate a greater quantity of vapor/aerosol. In these implementations, it should be appreciated that the duty cycle will be a function of inhalation strength. That is, taking the pattern in FIG. 6a as an example, the duty cycle may vary for both heating wires 43 between say 25% to 50%, where 50% is selected for the strongest possible inhalation (or at least an inhalation above a maximum threshold value) and 25% is selected for the weakest possible inhalation (or at least an inhalation strength equal to a threshold for detecting an inhalation). This may be applicable either when the duty cycles for both heating wires 43 are the same, or when the duty cycles are different (e.g., as in FIG. 6b), in which case the duty cycles may be varied to provide a certain ratio in the duty cycles between heating wire 43a and heating wire 43b.

It should also be appreciated that the total power supplied to the heating elements 43 may be dependent on a user input. For example, the device 1 may include a volume selection mechanism, which may be a button or switch (not shown) located on the reusable part 2 and which allows the user to select the quantity of aerosol produced. For instance, the volume selection mechanism may be a three position switch that can be actuated between a low, medium, or high setting where the low setting provides less aerosol to the user than the high setting and the medium setting provides a volume of aerosol somewhere between the volumes provided by the low and high settings. This may be the case when the power is supplied to the heating elements 43 via a user actuated button which, when pressed, supplies power to the heating elements 43. In this case, the volume selection mechanism controls the total power supplied to the heating elements 43 when the user actuates the power supply button. In a similar way as described above, the duty cycles are varied depending upon the setting of the volume selection mechanism.

In another aspect of the present disclosure, power may be distributed between the cartomizers 4 to reduce the chance of dry-out. As described above, drying-out should be avoided in order to maintain a consistent user experience when using the device 1. One way this can be controlled is via controlling the aerosol flow through each of the cartomizers 4; however one can alternatively (or additionally) control the power supplied to each of the cartomizers 4.

For example, in one implementation, the control circuitry 22 is configured to determine the quantity of source liquid stored in each of the liquid reservoirs 41, as described above in relation to the flow restriction members 25 (e.g., via capacitive plates detecting a change in capacitance as the source liquid is used up).

The control circuitry 22 is then configured to determine the power to be supplied to the respective cartomizers 4 based on the detected source liquid level (that is, the control circuitry 22 receives a signal or signals indicative of the sensed liquid level). In essence, the control circuitry 22 is configured to supply power such that the liquid reservoirs 41 will fully deplete at the same point in time in the future by adjusting the rate at which the source liquid is being used (or more accurately vaporized) by the device 1. For example, suppose cartomizer 4a contains 1 ml of source liquid while cartomizer 4b contains 0.5 ml of liquid. In this case, the source liquid in cartomizer 4b should be vaporized (consumed/depleted) at half the rate of the source liquid in cartomizer 4a in order for the cartomizers to be fully deplete at the same time in the future. The term "same time in the future" here should be understood to mean a point in time, either exactly or within a certain tolerance. For example, this may be based on a range within time, e.g., within 1 second or within 1 minute, etc., or within a certain number of puffs, e.g., within 1 puff or 2 puffs, etc. Equally, "fully depleted" should be understood to mean where no aerosol precursor remains or a small amount of aerosol precursor remains, e.g., less than 5%, 2%, or 1% of the maximum volume of aerosol forming material that can be stored in the cartomizer 4.

This rate is dependent (at least in part) on the power supplied to the heating elements 43. Accordingly, the control circuitry 22 is configured to calculate a power to be supplied to the respective cartomizers 4 such that the rate at which the cartomizers vaporize the source liquid means the remaining liquid will be consumed at the same point in time in the future. This means that the likelihood of the user experiencing a foul taste resulting from one of the cartomizers heating/burning a dry wicking element 42 while the other cartomizer continues to produce aerosol is reduced.

Generally speaking, the control circuitry 22 will supply a greater proportion of the power to the heating element 43 of the cartomizer 4 that comprises the greatest quantity of source liquid; that is, a greater power/average voltage will be supplied to cartomizer 4a. For example, if approximately 3 Watts is supplied to cartomizer 4b, then 6 Watts will be supplied to cartomizer 4a.

In one implementation, the control circuitry 22 is configured to continually determine the quantities of liquid within the cartomizers during use of the device 1. For example, the control circuitry 22 may receive a continuous measurement of the source liquid levels in the cartomizers (e.g., from the capacitive sensor) or the control circuitry may periodically receive a signal from the sensor. Based on the received signal, the control circuitry may increase or decrease the power supplied to the cartomizers accordingly. The control circuitry is configured to decrease the power supplied to the atomization unit of the cartomizer that comprises the smallest quantity of source liquid and/or increase the power supplied to the atomization unit of the cartomizer that comprises the greatest quantity of source liquid relative to the power supplied prior to the update. The control unit may proportion the power based on a certain total power (which may affect the volume of aerosol produced). For instance, using the above example, a total of 9 Watts is supplied to both cartomizers to generate a certain quantity of vapor, and during use the control circuitry 22 may determine that cartomizer 4b is not using the liquid quickly enough (and so cartomizer 4a will dry out more quickly). The control circuitry 22 is configured to alter the power supplied to cartomizer 4b from 3 W to 4 W, for example, and subsequently decrease the power supplied to cartomizer 4a from 6 W to 5 W. It should be appreciated that there may be no requirement to maintain a continuous total power, however, and so the control circuitry may instead increase/decrease the power to one or the other of the cartomizers.

It should be appreciated that while the above has described the reduction of the chance of one cartomizer drying-out before the other using power distribution, the skilled person will appreciate that this can also be achieved via additionally controlling air flow through the cartomizers (as described above). In this regard, the control circuitry 22 is configured to take into account the degree at which the flow restriction members 25 are open (and so the airflow rate through each of the cartomizers) before setting the proportion of power to be distributed to the different atomization units. This can offer an increased level of flexibility when preventing one cartomizer drying out before the other and may also offer a reduced impact on the users taste/experience of the aerosol (e.g., by altering the relative concentrations of the aerosols).

Another aspect of the present disclosure is the provision of two separate aerosol pathways, which are defined here as pathways that transport generated aerosol from the aerosol generating components, such as cartomizers 4, in the aerosol generating areas.

As mentioned previously, the example aerosol provision device 1 of FIGS. 1 and 2 generally provides two routes through which air/aerosol may pass through the device. For example, a first route starts from air inlet 23, passes along air channel 26 and through flow restriction member 25*a*, then passes into the receptacle 24*a* and through the cartomizer channel 44*a* of the first cartomizer 4*a*, into the receptacle 32*a*, along the mouthpiece channel 33*a* of the mouthpiece part 3 to the opening 31*a*. A second route starts from air inlet 23, passes along air channel 26 and through flow restriction member 25*b*, then passes into the receptacle 24*b* and through the cartomizer channel 44*b* of the second cartomizer 4*b*, into the receptacle 32*b*, along the mouthpiece channel 33*b* of the mouthpiece part 3 and to the opening 31*b*.

Each of the first and second routes through the device share a common component upstream of the flow restriction members 25 (namely, air channel 26 which is coupled to air inlet 23) but branch off from this common component. An aerosol pathway is defined in the present disclosure as a pathway starting from the component responsible for generating the aerosol/vapor. In the present example device 1, these are heating wires 43*a* and 43*b* of the cartomizers 4. It should be appreciated that these are the components along the first and second routes that first generate vapor from vaporizing the source liquid and, as such, any air flowing downstream of this point along the first and second routes is a combination/mixture of air and the generated vapor—that is, an aerosol. Accordingly, a first aerosol pathway and a second aerosol pathway can be defined within the device 1. That is, the first aerosol pathway first aerosol pathway starts from heating element 43*a*, passes through cartomizer channel 44*a* of the first cartomizer 4*a*, into the receptacle 32*a* and along the mouthpiece channel 33*a* of the mouthpiece part 3 to the opening 31*a*. The second aerosol pathway starts from heating element 43*b* passes through the cartomizer channel 44*b* of the second cartomizer 4*b*, into the receptacle 32*b* and along the mouthpiece channel 33*b* of the mouthpiece part 3 to the opening 31*b*.

As should be appreciated from FIGS. 1 and 2, the first and second aerosol pathways are physically isolated from one another downstream of the atomization unit. More specifically, aerosol generated from passing by heating element 43*a* and aerosol generated from passing by heating element 43*b* are not permitted to mix within the device during normal use. Instead, the individual aerosols exit the device 1 through the respective mouthpiece openings 31*a* and 31*b* and initially are separate from one another immediately after exiting the device 1. The fact that the aerosols are physically isolated from one another when passing through the device 1 can lead to different user experiences when receiving the separate aerosol as compared to inhaling aerosols that are mixed within the device. The term “in normal use” should be understood to mean “as a user inhales normally on the device” and thus, specifically, we refer here to the normal route through the device that the aerosol would take when a user inhales in this way. This should be distinguished from abusive behavior, e.g., exhaling into the device rather than inhaling (for example). In normal use, the present disclosure describes arrangements in which the different aerosols are isolated downstream of the point at which the aerosol is generated.

Aerosols exiting the device can be mixed to provide a combination of the aerosols to the user predominately via two methods. The first method involves the different aerosols exiting the device 1 separately from one another and, as the user further inhales and draws the aerosols into the user's oral cavity, the two aerosols may mix in the user's oral cavity before impacting on a surface of the oral cavity (e.g., the tongue or inner surface of the cheeks) where the mixture of aerosols is then received by the user. It should also be pointed out that mixing may occur at other points after the oral cavity along the user's respiratory organs, e.g., in the throat, esophagus, lungs etc. The second method involves keeping the aerosols substantially separate such that each aerosol predominately impacts a different area of the user's mouth (e.g., such as the left and right inner surfaces of the cheeks). Here the mixing is performed by the user's brain combining the different signals resulting from receiving the aerosols in different parts of the mouth. Generally, both of these techniques here are referred to as “mixing in the mouth” as opposed to mixing in the device. It should be appreciated that in practice the different aerosols that are inhaled will likely mix via both of the two methods; however, depending on the configuration of the mouthpiece part 3, the mixing may occur predominately via one of the methods described above.

The mouthpiece part 3 shown in FIGS. 1 and 2 provides the mouthpiece channels 33 in such that the axes of the channels 33 converge at a point away from the top end of the device 1. In other words, assuming the mouthpiece part defines an axis that extends from the bottom end to the top end of the device and passes generally through the center of the mouthpiece part, the aerosols are configured to be directed toward the axis. Generally, this mouthpiece part 3 may be considered to mix aerosols predominately according to the first method described above, namely via mixing of the aerosols before the impacting a surface of the user's mouth.

FIG. 7*a* schematically shows another exemplary mouthpiece part 103 configured to fit/couple to control part 2. FIG. 7*a* shows the mouthpiece part 103 in cross-section on the left hand-side and on the right hand-side of FIG. 7*a* is shown the mouthpiece part 103 as viewed in a direction along a longitudinal axis of the mouthpiece part 103. Mouthpiece part 103 is substantially the same as mouthpiece part 3 with the exception that ends of the mouthpiece channels 133*a* and 133*b* are provided such that they divert away from the general longitudinal axes of the mouthpiece channels 133. Accordingly, the mouthpiece openings 131*a* and 131*b* are provided at positions closer to the left and right sides of the mouthpiece part 103 as compared to openings 31*a* and 31*b* of mouthpiece part 3. The longitudinal axes of the end parts of the mouthpiece channels 133 converge at a point within the device 1 (in contrast to mouthpiece part 3). That is, the channels 133 are configured to divert the separate aerosols away from the longitudinal axis of the mouthpiece part 103. Generally, this mouthpiece part 103 may be considered to mix aerosols predominately according to the second method described above, namely via mixing of the aerosols after each separate aerosol impacts a surface of the user's mouth. In other words, mouthpiece part 103 can be considered to direct or target the different aerosols to different parts of the user's mouth.

Figure 7A:
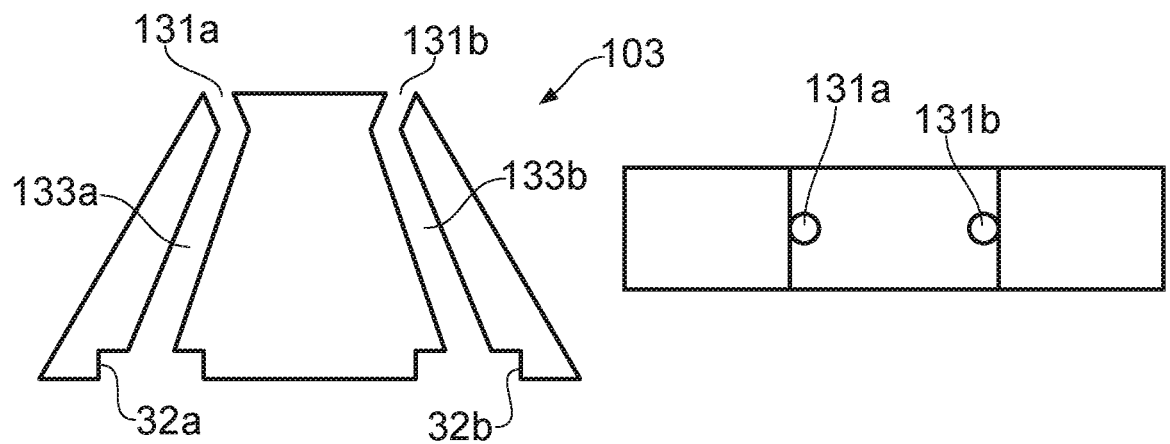
FIG. 7a schematically illustrates an exemplary mouthpiece part for use with the control part 2 of FIGS. 1 and 2 in which aerosol generated from each cartomizer is separately directed towards different sides of a user's mouth when a user inhales on the system.
Figure 7B:
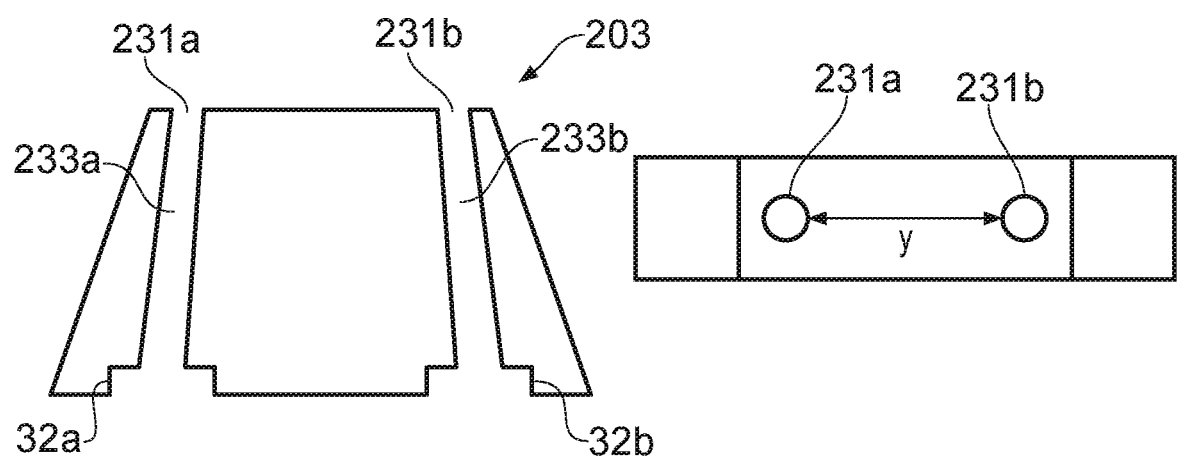
FIG. 7b schematically illustrates another exemplary mouthpiece part for use with the control part 2 of FIGS. 1 and 2 in which aerosol generated from each cartomizer is separately directed towards mouthpiece openings on a surface of the mouthpiece part spaced apart from one another to enable a user to inhale through one or both of the mouthpiece openings.

FIG. 7b schematically shows another exemplary mouthpiece part 203 configured to fit/couple to control part 2. FIG. 7b shows the mouthpiece part 203 in cross-section on the left hand-side and on the right hand-side of FIG. 7b is shown the mouthpiece part 203 as viewed in a direction along the longitudinal axis of the mouthpiece part 203. Mouthpiece part 203 is substantially the same as mouthpiece part 3 with the exception that the mouthpiece channels 233a and 233b are provided at a shallower angle relative to the longitudinal axis of the device 1. That is longitudinal axes of mouthpiece channels 233 converge at a point further way from the device 1 as compared to mouthpiece part 3. The mouthpiece openings 231a and 231b are subsequently separated by a greater distance, indicated as separation distance y in FIG. 7b. Note also that the width of the top end of the mouthpiece part 203 is greater than the width of the top end of mouthpiece part 3, e.g., the width of mouthpiece part 203 is around 4 cm. This arrangement means that the degree of mixing of the aerosols is less than with mouthpiece part 3. Additionally, by providing a suitable separation distance y between the mouthpiece openings 231 of, for example, between 2 cm to 4 cm, e.g. 3.5 cm, the user is able to selectively inhale from mouthpiece opening 231a, mouthpiece opening 231b or a combination of mouthpiece openings 231a and 231b by positioning their mouth over the corresponding mouthpiece opening(s) 231. That is, the user can choose which of the aerosols they receive (and hence which of the heating wires 43a, 43b of the cartomizers 4 are supplied with power). More generally, the mouthpiece openings 231 are provided at positions on the mouthpiece part 3 which allow the user to selectively inhale from the mouthpiece openings 231.

Figure 7C:
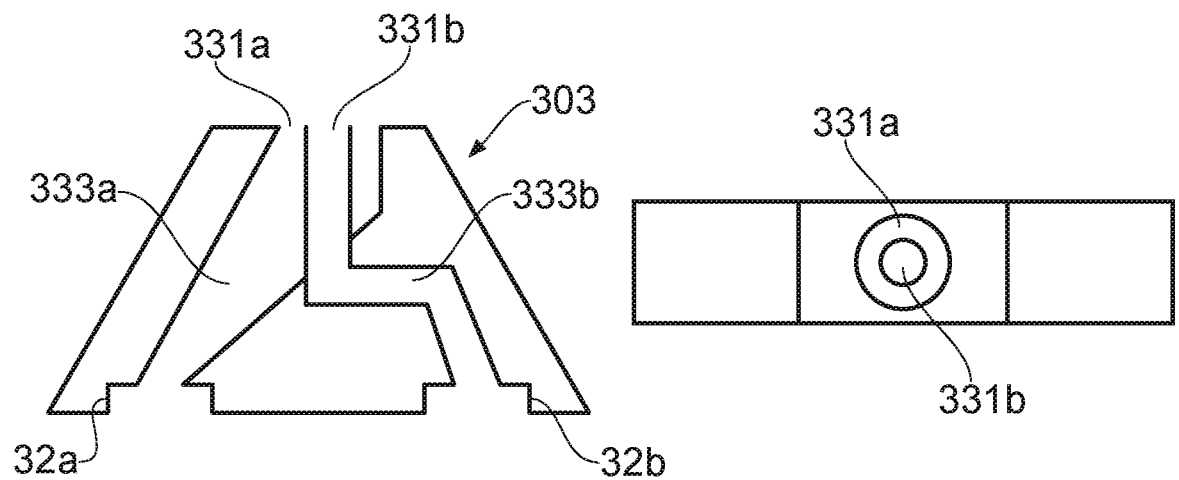
FIG. 7c schematically illustrates yet another exemplary mouthpiece part for use with the control part 2 of FIGS. 1 and 2 in which aerosol generated from each cartomizer is separately directed towards different mouthpiece openings but in which the mouthpiece openings are concentrically arranged.

FIG. 7c schematically shows another exemplary mouthpiece part 303 configured to fit/couple to control part 2. FIG. 7c shows the mouthpiece part 303 in cross-section on the left hand-side and on the right hand-side of FIG. 7c is shown the mouthpiece part 303 as viewed in a direction along the longitudinal axis of the mouthpiece part 303. Mouthpiece part 303 is substantially the same as mouthpiece part 3 with the exception that the mouthpiece channels 333a and 333b are configured to provide different sized, and in this case also concentric, mouthpiece openings 331a and 331b. More specifically, it can be seen that mouthpiece opening 331a surrounds the outer diameter of mouthpiece opening 331b. In this regard[,] it should be appreciated that mouthpiece channel 333b includes a walled section which extends into the hollow portion of mouthpiece channel 333a (e.g., mouthpiece channel 333b includes a vertically extending tubular wall which partitions channel 333a from 333b). This configuration provides the second aerosol surrounded by the first aerosol as the aerosols exit the mouthpiece part 303. The majority of the mixing may be performed via the first method above, however this configuration may also lead to situations where the first aerosol (that is, the aerosol generated from cartomizer 4a) impacts the user's mouth shortly before the second aerosol (that is, the aerosol generated from cartomizer 4b). This can lead to a different user experience, e.g., a gradual reception/transition from the first to the second aerosol.

Figure 7D:
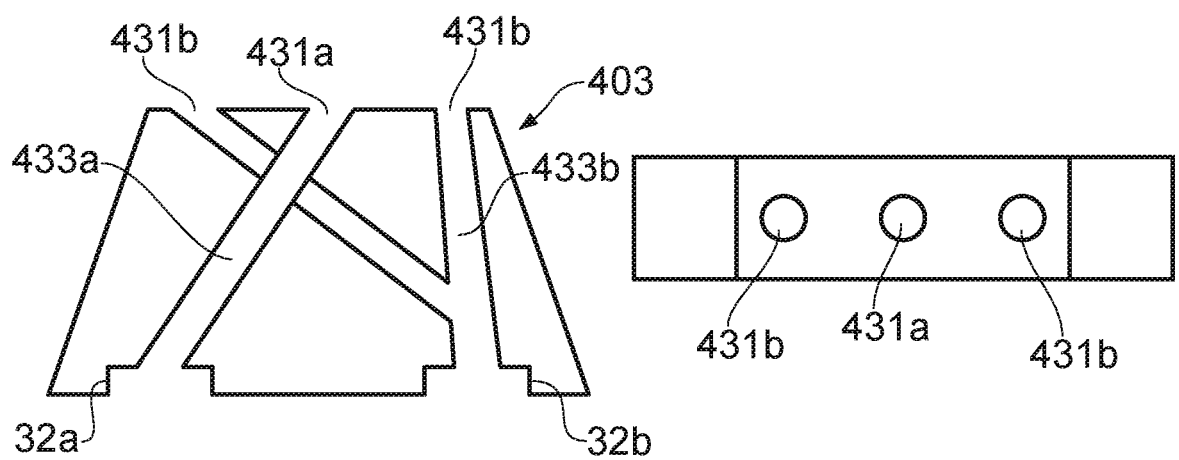
FIG. 7d schematically illustrates a further exemplary mouthpiece part for use with the control part 2 of FIGS. 1 and 2 in which aerosol generated from one cartomizer is directed towards multiple mouthpiece openings surrounding a mouthpiece opening to which aerosol generated from the other cartomizer is directed.

FIG. 7d schematically shows another exemplary mouthpiece part 403 configured to fit/couple to control part 2. FIG. 7d shows the mouthpiece part 403 in cross-section on the left hand-side of the Figure and on the right hand-side of FIG. 7d is shown the mouthpiece part 403 as viewed in a direction along the longitudinal axis of the mouthpiece part 403. Mouthpiece part 403 is substantially the same as mouthpiece part 3 with the exception that the mouthpiece channel 433b is split into two channels coupling to two mouthpiece openings 431b. Specifically, the mouthpiece openings are arranged such that openings 431b fluidly connected to cartomizer 4b are provided either side of the mouthpiece opening 431a fluidly connected to cartomizer 4a. It should be noted that one branch of mouthpiece channel 433b is shaped to pass overtop (or underneath) the mouthpiece channel 433a This can provide a different user experience by directed the aerosol generated from cartomizer 4b towards the outer portions of the user's mouth while directing the aerosol generated form cartomizer 4a towards the middle of the oral cavity.

In general, in view of FIGS. 7a to 7d and the mouthpiece part 3 of FIGS. 1 and 2, it can be seen that the mouthpiece part of the aerosol provision device 1 can be arranged in a variety of ways to achieve mixing of the different aerosols within the mouth of a user of the device 1 to provide the user with different user experiences. In each of the examples shown, the aerosols are prevented from mixing within the device, in normal use. While the above mentioned Figures show specific designs of the mouthpiece parts, it should be appreciated that the mouthpiece channels may take any configuration necessary or desired in order to realize the intended functions of either mixing aerosols within the oral cavity or targeting aerosols to certain regions of the oral cavity.

Figure 8A:
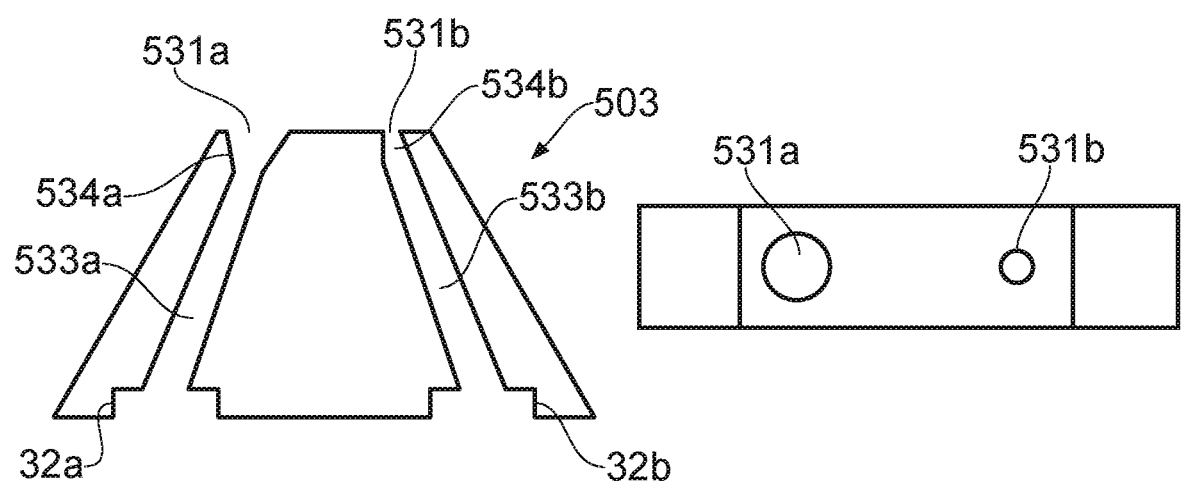
FIG. 8a schematically illustrates an exemplary mouthpiece part for use with the control part 2 of FIGS. 1 and 2 in which mouthpiece channels include end sections configured to alter the properties of aerosol passing through the channels.
Figure 8B:
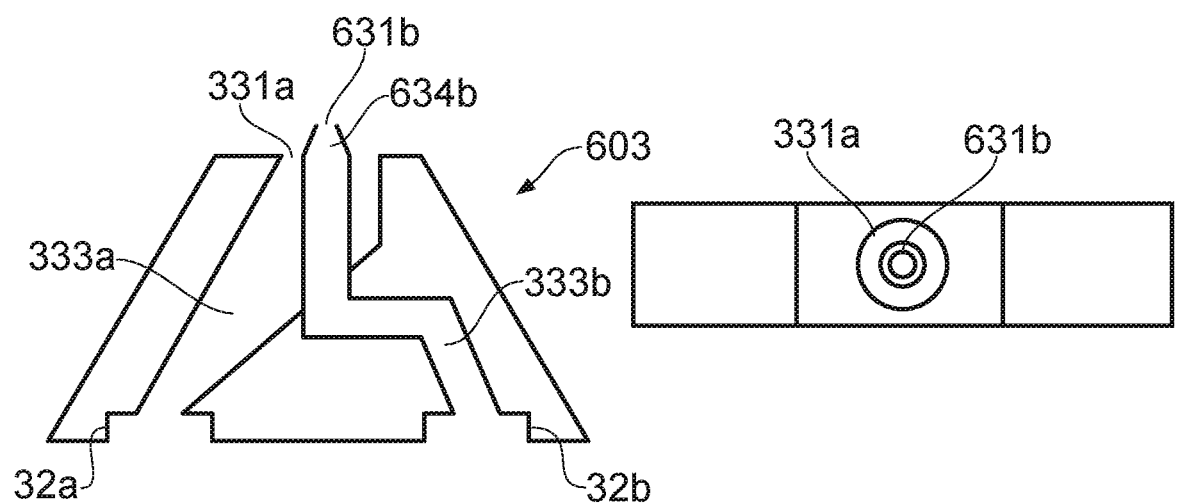
FIG. 8b schematically illustrates a further exemplary mouthpiece part for use with the control part 2 of FIGS. 1 and 2 in which a mouthpiece channel includes an end section that protrudes from the surface of the mouthpiece part and is configured to alter the properties of aerosol passing through the channel.

FIGS. 8a and 8b schematically show alternative arrangements of mouthpiece parts 503 and 603. In these figures, the mouthpiece parts are provided with modified ends of the various mouthpiece channels in order to provide the aerosol streams with different properties, specifically different densities.

FIG. 8a schematically shows an exemplary mouthpiece part 503 configured to fit/couple to control part 2. FIG. 8a shows the mouthpiece part 503 in cross-section on the left hand-side and on the right hand-side of FIG. 8a is shown the mouthpiece part 503 as viewed in a direction along the longitudinal axis of the mouthpiece part 503. Mouthpiece part 503 is substantially the same as mouthpiece part 3. However, mouthpiece channels 533a and 533b are provided with end sections 543 that provide a widening or narrowing of the mouthpiece channel 533 towards the top end of the mouthpiece part 503.

More specifically, mouthpiece channel 533a includes an end section 534a in which the diameter of the mouthpiece channel 533a gradually increases in the downstream direction. This results in a relatively large diameter mouthpiece opening 531a. As aerosol generated from cartomizer 4a is inhaled along mouthpiece channel 533a by the user's puffing action, the density of the aerosol gradually decreases as the aerosol moves through end section 534a. This leads to aerosol expelled from the mouthpiece opening 531a that is relatively diffuse compared to aerosol expelled from mouthpiece opening 31a, for example. Generally speaking, a mouthpiece channel including an end section which increases in diameter (or width/thickness) towards the point where aerosol exits the device 1 provides a more diffuse aerosol stream.

Conversely, mouthpiece channel 533*b* includes an end section 534*b* in which the diameter of the mouthpiece channel 533*b* gradually decreases in the downstream direction. This results in a relatively small diameter mouthpiece opening 531*b*. As aerosol generated from cartomizer 4*b* is inhaled along mouthpiece channel 533*b* by the user's puffing action, the density of the aerosol gradually increases as the aerosol moves through end section 534*b*. This leads to a more concentrated jet of aerosol being expelled from the mouthpiece opening 531*b* compared to aerosol expelled from mouthpiece opening 31*b*, for example. Generally speaking, a mouthpiece channel including an end section which decreases in diameter (or width/thickness) towards the point where aerosol exits the device 1 provides a more jet-like concentrated aerosol stream (or a less diffuse aerosol stream).

It should be appreciated that although FIG. 8*a* shows the end sections 534 of each mouthpiece channel 533 located below the top end of the mouthpiece part (that is, below the uppermost surface), the mouthpiece channels[,] and hence the end section[,] may extend beyond the top end of the mouthpiece part. For example, FIG. 8*b* schematically shows a modified version of mouthpiece part 303 shown in FIG. 7*c*. FIG. 8*a* shows the mouthpiece part 603 in cross-section on the left hand-side and on the right hand-side is shown the mouthpiece part 603 as viewed in a direction along the longitudinal axis of the mouthpiece part 603. In this arrangement, mouthpiece channel 333*b* is additionally provided with end portion 634*b* that extends/protrudes from the end of mouthpiece channel 333*b*. The end section 634*b* may be a separate component fitted to the end of mouthpiece channel 333*b*, or end section 634*b* may be integrally formed with the mouthpiece channel 333*b* (in essence providing an extension to mouthpiece channel 333*b*). End section 634*b* is provided with walls that narrow in diameter in a downstream direction, and so aerosol expelled from the end section is more jet-like (i.e., it has a higher source liquid particle density).

The above examples show how end sections of the mouthpiece channel may be formed in order to give different properties to the aerosol that is expelled from that mouthpiece channel. However, it should be appreciated that the entire mouthpiece channel, as opposed to merely an end section, can be formed to give different properties to the aerosol. For example, the channel 533*b* in FIG. 8*a* could alternatively be configured to gradually decrease in diameter from the connection to receptacle 32*b* through to opening 531*b* in order to a provide a jet-like aerosol stream. It should also be appreciated that in other embodiments the mouthpiece channels may be provided with additional components (e.g., a baffle plate) to adjust the properties of the aerosol exiting the channel.

It should also be appreciated that while the above examples have generally focused on providing different aerosol streams that mix in the mouth of a user and, in some cases, that are targeted to different regions of the mouth, in some implementations the different aerosol streams may be targeted to completely different regions of the user's respiratory system. For example, aerosol generated by cartomizer 4*a* may be targeted to deposit in the oral cavity of the user's mouth (which may be achieved using a mouthpiece channel shaped such as channel 533*a* to provide a diffuse cloud-like aerosol within the oral cavity), whereas aerosol generated from cartomizer 4*b* may be targeted to deposit in the lungs of the user's respiratory system (which may be achieved using a mouthpiece channel shaped such as channel 533*b* to provide a jet-like stream of aerosol which travels generally deeper into the respiratory system with relatively less dispersion). Such an arrangement could be used to deliver a flavored aerosol to the user's mouth and a nicotine containing aerosol to the user's lungs, for example. Alternatively and/or additionally, the system could be configured to produce multiple aerosols with differing particle size distributions.

The term aerosol generating component has generally been exemplified throughout by a cartomizer 4, where the cartomizer includes both a source liquid (or more generally an aerosol precursor material) and an atomizing unit. More generally the term aerosol generating component refers to components that allow for the generation of aerosol when present in the device 1.

For example, it has been described above that the control part 2 receives a plurality of cartomizers 4, where the cartomizers 4 include the liquid reservoir 41 and an atomization unit, which is described above as including a wicking element 42 and a heating element 43. In this regard, a cartomizer is considered herein to be a cartridge that includes an atomization unit. It should be appreciated that in some implementations, the atomization unit is alternatively provided in the control part 2 of the aerosol provision device 1. In this case, instead of cartomizers being inserted into the receptacles 24 of the device 1, cartridges (which do not include an atomization unit) can be inserted into the receptacles of the device. The cartridges can be configured to mate with the atomization unit in a suitable way depending on the type of atomization unit installed. For example, if the atomization unit comprises a wicking element and a heating element, the wicking element can be configured to fluidly communicate with the source liquid contained in the cartridge. Hence, in implementations where the control part 2 is arranged to receive a cartridge, the cartridge is considered to be the aerosol generating component.

It has also been described above that cartomizers/cartridges include a liquid reservoir containing a source liquid which acts as a vapor/aerosol precursor. However, in other implementations, the cartomizers/cartridges may contain other forms of vapor/aerosol precursor, such as tobacco leaves, ground tobacco, reconstituted tobacco, gels, etc. It should also be understood that any combination of cartridges/cartomizers and aerosol precursor materials can be implemented in the above described aerosol provision system. For example, cartomizer 4*a* may include a liquid reservoir 41 and source liquid, while cartomizer 4*b* may include reconstituted tobacco and a tubular heating element in contact with the reconstituted tobacco. It should be appreciated that any suitable type of heating element (or more generally atomizing unit) may be selected in accordance with aspects of the present disclosure, e.g., a wick and coil, an oven-type heater, an LED type heater, a vibrator, etc.

It has also been described that the aerosol provision device 1 is capable of receiving aerosol generating components, e.g., two cartomizers 4. However, it should be appreciated that the principles of the present disclosure can be applied to a system configured to receive more than two aerosol generating components, e.g., three, four, etc. cartomizers.

In other implementations in accordance with certain aspects of this disclosure, the aerosol generating areas, i.e., receptacles 24, are instead configured to receive a quantity of aerosol precursor material directly, e.g., a quantity of source liquid. That is, the aerosol generating areas are configured to receive and/or hold the aerosol precursor material. As such, the aerosol generating component is considered to be the aerosol precursor material. In these implementations, the atomization unit is provided in the control part 2 such that it is able to communicate with the aerosol precursor material in the receptacle 24. For example, the aerosol generating areas, e.g. receptacles 24, may be configured to act as liquid reservoirs 41 and be configured to receive a source liquid (the aerosol generating component). An atomizing unit, including a wicking material and a heating element, is provided in or adjacent the receptacle 24 and thus liquid can be transported to the heating element and vaporized in a similar manner to that described above. In these implementations, however, the user is able to re-fill (or re-stock) the receptacles with the corresponding aerosol precursor material. It should also be appreciated that the receptacles may receive a wadding or similar material soaked in a source liquid, with the wadding being placed in contact with/proximal to an atomizing unit.

It has also been described above that the mouthpiece part 3 is a separate component to the control part 2. In some cases, a plurality of mouthpiece parts 3 having different shaped mouthpiece channels 33 may be supplied to the user; for example, the user may be supplied with mouthpiece parts 3, 103, 203, etc. The user is able to swap which mouthpiece parts 3, 103, 203 is coupled to the control part 2 in order to alter the mixing of the aerosols (and more generally the user experience). However, it should be appreciated in some implementations, the mouthpiece part 3 may be coupled to the control part 2 in any suitable manner, e.g., via a hinge or via a tether.

Thus, there has been described an aerosol provision device for generating aerosol to be inhaled by a user from a plurality of discrete aerosol generating areas each containing an aerosol generating component, the aerosol provision device comprising: a mouthpiece from which a user inhales generated aerosol during use; a first flow pathway arranged to pass through a first aerosol generating area and fluidly connected to the mouthpiece; and a second flow pathway arranged to pass through a second aerosol generating area and fluidly connected to the mouthpiece, wherein the first and second flow pathways are each provided with a flow restriction member configured to vary the flow of air through the respective flow pathways based on the presence of an aerosol generating component in the respective aerosol generating areas in the device and/or a parameter associated with the respective aerosol generating component in the device.

Thus, there has been described an aerosol provision device for generating aerosol for user inhalation, the aerosol provision device comprising: a first aerosol generating area and a second aerosol generating area each for receiving an aerosol precursor material; a mouthpiece from which a user inhales generated aerosol during use, wherein the mouthpiece comprises first and second mouthpiece openings; a first pathway extending from the first aerosol generating area to the first mouthpiece opening for transporting a first aerosol generated from the aerosol precursor material in the first aerosol generating area; and a second pathway extending from the second aerosol generating area chamber to the second mouthpiece opening for transporting a second aerosol generated from the aerosol precursor material in the second aerosol generating area, wherein the first and second pathways are physically isolated from one another to prevent mixing of the first and second aerosols as the first and second aerosols are transported along the respective pathways.

Thus, there has been described an aerosol provision device for generating aerosol from a plurality of aerosol generating areas each configured to receive an aerosol precursor material, wherein the aerosol provision device comprises: a power source for providing power to a first atomizing element configured to generate aerosol from a first aerosol precursor material present in the first aerosol generating area and to a second atomizing element configured to generate aerosol from a second aerosol precursor material present in a second aerosol generating area; and power distribution circuitry configured to distribute power between the first and second atomizing elements based on at least one parameter of aerosol precursor material currently present in the first and second aerosol generating areas respectively.

While the above described embodiments have in some respects focused on some specific example aerosol provision systems, it will be appreciated the same principles can be applied for aerosol provision systems using other technologies. That is to say, the specific manner in which various aspects of the aerosol provision system function are not directly relevant to the principles underlying the examples described herein.

In order to address various issues and advance the art, this disclosure shows by way of illustration various embodiments in which the claimed disclosure(s) may be practiced. The advantages and features of the disclosure are of a representative sample of embodiments only, and are not exhaustive and/or exclusive. They are presented only to assist in understanding and to teach the claimed disclosure(s) It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An aerosol provision device for generating aerosol from a plurality of aerosol generating areas each configured to receive an aerosol precursor material, wherein the aerosol provision device comprises:
   a power source for providing power to a first atomizing element configured to generate aerosol from a first aerosol precursor material present in a first aerosol generating area of the plurality of aerosol generating areas and to a second atomizing element configured to generate aerosol from a second aerosol precursor material present in a second aerosol generating area of the plurality of aerosol generating areas; and
   power distribution circuitry configured to distribute power between the first atomizing element and the second atomizing element based on at least one parameter of the first aerosol precursor material and the second aerosol precursor material currently present in the first aerosol generating area and the second aerosol generating area, respectively, wherein the power is distributed between the first atomizing element and the second atomizing element so as to generate aerosol from the first aerosol precursor material and the second aerosol precursor material;

wherein the at least one parameter is a quantity of aerosol precursor material, and wherein the power distribution circuitry is configured to distribute power to the first atomizing element and the second atomizing element such that a rate of atomization of the aerosol precursor material present in the first aerosol generating area or the second aerosol generating area having a lower quantity of aerosol precursor material is lower than a rate of atomization of the aerosol precursor material present in the first aerosol generating area or the second aerosol generating area having a higher quantity of aerosol precursor material.

2. The aerosol provision device of claim 1, wherein the power distribution circuitry is configured to supply a greater proportion of power to the first atomizing element or the second atomizing element of the first aerosol generating area or the second aerosol generating area that comprises a greatest quantity of aerosol precursor material.

3. The aerosol provision device of claim 1, wherein power is supplied to the first atomizing element and the second atomizing element such that the first aerosol precursor material and the second aerosol precursor material within the first aerosol generating area and the second aerosol generating area will fully deplete at the same time.

4. The aerosol provision device of claim 1, wherein the at least one parameter is a presence of a first aerosol generating component or a second aerosol generating component comprising the first aerosol precursor material or the second aerosol precursor material, respectively, in the respective first aerosol generating area or the second aerosol generating area.

5. The aerosol provision device of claim 4, wherein the power distribution circuitry is configured to increase the power supplied to the first atomizing element in an absence of the second aerosol generating component in the second aerosol generating area relative to when the second aerosol generating component is present in the second aerosol generating area.

6. The aerosol provision device of claim 4, wherein the power distribution circuitry is configured to distribute increased power to the first atomizing element in an absence of the second aerosol generating component such that a volume of aerosol produced is substantially the same as a distribution of power when both the first aerosol generating component and the second aerosol generating component are present.

7. The aerosol provision device of claim 4, wherein the power distribution circuitry is configured to distribute increased power to the first atomizing element in an absence of the second aerosol generating component such that a concentration of vaporized particles to air is substantially the same as a distribution of power when both the first aerosol generating component and the second aerosol generating component are present.

8. The aerosol provision device of claim 5, wherein a difference in a volume of aerosol or a concentration of vaporized particles to air produced between when the first aerosol generating component and the second aerosol generating component are both present in the aerosol provision device and when the second aerosol generating component is not present is less than 20%.

9. The aerosol provision device of claim 5, wherein the power supplied to the first atomizing element when the second aerosol generating component is not present in the aerosol provision device is double the power supplied to the first atomizing element when the second aerosol generating component is present in the device.

10. The aerosol provision device of claim 1, wherein the aerosol provision device is configured to determine the at least one property based on a change in an electrical property of the aerosol provision device.

11. The aerosol provision device of claim 1, wherein the power distribution circuitry is configured to alter the distribution of power between the first atomizing element and the second atomizing element during use of the aerosol provision device.

12. The aerosol provision device of claim 11, wherein the power distribution circuitry is configured to alter the power distribution based on a set total power, wherein the power distribution circuitry is configured to decrease the power supplied to the first atomizing element or the second atomizing element of the first aerosol generating area or the second aerosol generating area that comprises a smallest quantity of aerosol precursor material and increase the power supplied to the first atomizing element or the second atomizing element of the first aerosol generating area or the second aerosol generating area that comprises a greatest quantity of aerosol precursor material by the same amount.

13. The aerosol provision device of claim 1, wherein the power distribution circuitry is configured to distribute power to the first atomizing element and the second atomizing element additionally based on a flow of air through the first aerosol generating area and the second aerosol generating area.

14. The aerosol provision device of 1, wherein the power distribution circuitry is configured to supply power to the first atomizing element and the second atomizing element based using a pulse width modulation technique, wherein power is supplied to the second atomizing element during an off phase of a duty cycle of the first atomizing element.

15. The aerosol provision device of claim 1, wherein a total power supplied is determined based on a strength of an inhalation performed by the user as the user inhales on the aerosol provision device.

16. The aerosol provision device of claim 1, wherein a total power supplied is determined based on a user actuatable mechanism configured to allow the user to select between a plurality of different power settings.

17. An aerosol provision system for generating aerosol from a plurality of aerosol generating areas each configured to receive an aerosol precursor material, the system comprising:

the aerosol provision device of claim 1; and the first aerosol precursor material, wherein the first aerosol precursor material is located in the first aerosol generating area.

18. The system of claim 17, further comprising the second aerosol precursor material, wherein the second aerosol precursor material is located in the second aerosol generating area.

19. The system of claim 18, wherein the first aerosol precursor material is housed within a first cartridge forming the first aerosol generating component and the second aerosol precursor material is housed within a second cartridge forming the second aerosol generating component, and wherein the first aerosol generating area and the second aerosol generating area are configured to receive the first aerosol generating component and the second aerosol generating component, respectively.

20. A method of power distribution in an aerosol provision device for generating aerosol from a first aerosol generating area configured to receive a first aerosol precursor material and a second aerosol generating area configured to receive a second aerosol precursor material, the method comprising:
- receiving an indication of at least one parameter of a quantity of aerosol precursor material currently present in at least one of the first aerosol generating area or the second aerosol generating area, respectively; and
- distributing power between a first atomization element configured to generate aerosol from the first aerosol precursor material and a second atomization element configured to generate aerosol from the second aerosol precursor material based on the received indication, wherein the power is distributed between the first atomizing element and the second atomizing element so as to generate aerosol from the first aerosol precursor material and the second aerosol precursor material;
- wherein the at least one parameter is a quantity of aerosol precursor material, and wherein the power distribution circuitry is configured to distribute power to the first atomizing element and the second atomizing element such that a rate of atomization of the aerosol precursor material present in the first aerosol generating area or the second aerosol generating area having a lower quantity of aerosol precursor material is lower than a rate of atomization of the aerosol precursor material present in the first aerosol generating area or the second aerosol generating area having a higher quantity of aerosol precursor material.

21. An aerosol provision means for generating aerosol from a plurality of storage means each configured to receive an aerosol precursor material, wherein the aerosol provision means comprises:
- power means for providing power to a first atomizing means configured to generate aerosol from a first aerosol precursor material present in the first storage means and to a second atomizing means configured to generate aerosol from a second aerosol precursor material present in a second storage means; and
- power distribution means configured to distribute power between the first atomizing means and the second atomizing means based on at least one parameter of aerosol precursor material currently present in the first storage means and the second storage means, respectively, wherein the power is distributed between the first atomizing element and the second atomizing element so as to generate aerosol from the first aerosol precursor material and the second aerosol precursor material;
- wherein the at least one parameter is a quantity of aerosol precursor material, and wherein the power distribution means is configured to distribute power to the first atomizing means and the second atomizing means such that a rate of atomization of the aerosol precursor material present in the first storage means or the second storage means having a lower quantity of aerosol precursor material is lower than a rate of atomization of the aerosol precursor material present in the first storage means or the second storage means having a higher quantity of aerosol precursor material.

* * * * *